(12) United States Patent
Duindam et al.

(10) Patent No.: US 11,937,880 B2
(45) Date of Patent: Mar. 26, 2024

(54) GRAPHICAL USER INTERFACE FOR MONITORING AN IMAGE-GUIDED PROCEDURE

(71) Applicant: INTUITIVE SURGICAL OPERATIONS, INC., Sunnyvale, CA (US)

(72) Inventors: Vincent Duindam, San Francisco, CA (US); Lauren L. Argo, San Francisco, CA (US); Cristian Bianchi, Mountain View, CA (US); Christopher R. Carlson, Belmont, CA (US); Energy Cruse, II, Foster City, CA (US); Scott S. Ichikawa, Seattle, WA (US); Aaron B. Tinling, Chimacum, WA (US); Oliver J. Wagner, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 839 days.

(21) Appl. No.: 16/499,575

(22) PCT Filed: Apr. 18, 2018

(86) PCT No.: PCT/US2018/028190
§ 371 (c)(1),
(2) Date: Sep. 30, 2019

(87) PCT Pub. No.: WO2018/195216
PCT Pub. Date: Oct. 25, 2018

(65) Prior Publication Data
US 2020/0054399 A1 Feb. 20, 2020

Related U.S. Application Data

(60) Provisional application No. 62/486,879, filed on Apr. 18, 2017.

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/10* (2016.02); *A61B 34/25* (2016.02); *A61B 34/35* (2016.02);
(Continued)

(58) Field of Classification Search
None
See application file for complete search history.

(56) References Cited

U.S. PATENT DOCUMENTS

| 5,638,819 A | 6/1997 | Manwaring et al. |
| 6,346,940 B1 | 2/2002 | Fukunaga |

(Continued)

FOREIGN PATENT DOCUMENTS

| CN | 101854853 A | 10/2010 |
| CN | 104780826 A | 7/2015 |

(Continued)

OTHER PUBLICATIONS

International Preliminary Report on Patentability for Application No. PCT/US2018/028190, dated Oct. 31, 2019, 11 pages.

(Continued)

*Primary Examiner* — Baisakhi Roy
*Assistant Examiner* — Kaitlyn E Sebastian
(74) *Attorney, Agent, or Firm* — Haynes & Boone, LLP

(57) ABSTRACT

A system and method of monitoring a procedure includes a medical device. The medical device includes an elongate device including a flexible body, a tracking system disposed along at least a portion of the flexible body, and one or more processors communicatively coupled to the tracking system. The one or more processors are configured to receive a route (Continued)

to a target location in an anatomy, determine one or more features of the route based on a first anatomical representation, generate a reduced anatomical representation based on the one or more features of the route, receive real-time position information from the tracking system, associate the real-time position information to the reduced anatomical representation, and dynamically display the reduced anatomical representation with the associated real-time position information.

19 Claims, 19 Drawing Sheets

(51) Int. Cl.
    *A61B 34/10*     (2016.01)
    *A61B 34/35*     (2016.01)
    *A61B 34/37*     (2016.01)
    *A61B 17/00*     (2006.01)
    *A61B 34/30*     (2016.01)

(52) U.S. Cl.
    CPC ............... *A61B 2017/00809* (2013.01); *A61B 2034/105* (2016.02); *A61B 2034/107* (2016.02); *A61B 2034/2051* (2016.02); *A61B 2034/2061* (2016.02); *A61B 2034/2074* (2016.02); *A61B 2034/252* (2016.02); *A61B 2034/254* (2016.02); *A61B 2034/301* (2016.02)

(56) References Cited

U.S. PATENT DOCUMENTS

| | | |
|---|---|---|
| 6,380,732 B1 | 4/2002 | Gilboa |
| 6,389,187 B1 | 5/2002 | Greenaway et al. |
| 6,432,041 B1 | 8/2002 | Taniguchi et al. |
| 6,671,538 B1 | 12/2003 | Ehnholm et al. |
| 7,316,681 B2 | 1/2008 | Madhani et al. |
| 7,772,541 B2 | 8/2010 | Froggatt et al. |
| 7,930,065 B2 | 4/2011 | Larkin et al. |
| 8,218,846 B2 | 7/2012 | Trumer et al. |
| 8,412,307 B2 | 4/2013 | Willis et al. |
| 8,672,836 B2 | 3/2014 | Higgins et al. |
| 8,900,131 B2 | 12/2014 | Chopra et al. |
| 9,259,274 B2 | 2/2016 | Prisco |
| 9,326,660 B2 | 5/2016 | Akimoto et al. |
| 9,452,276 B2 | 9/2016 | Duindam et al. |
| 9,603,668 B2 | 3/2017 | Weingarten et al. |
| 11,612,384 B2 | 3/2023 | Duindam et al. |
| 2002/0049375 A1* | 4/2002 | Strommer ............ A61B 8/0833 600/407 |
| 2004/0082849 A1 | 4/2004 | Schweikard et al. |
| 2004/0165810 A1 | 8/2004 | Fujita |
| 2005/0182295 A1 | 8/2005 | Soper et al. |
| 2005/0261550 A1 | 11/2005 | Akimoto et al. |
| 2006/0013523 A1 | 1/2006 | Childlers et al. |
| 2007/0065077 A1 | 3/2007 | Childers et al. |
| 2007/0270650 A1 | 11/2007 | Eno et al. |
| 2007/0293721 A1 | 12/2007 | Gilboa |
| 2008/0275467 A1 | 11/2008 | Liao et al. |
| 2009/0156895 A1 | 6/2009 | Higgins et al. |
| 2009/0198104 A1 | 8/2009 | Sugiyama |
| 2009/0227861 A1 | 9/2009 | Ganatra et al. |
| 2009/0326553 A1 | 12/2009 | Mustufa et al. |
| 2010/0076305 A1 | 3/2010 | Maier-Hein et al. |
| 2010/0141675 A1 | 6/2010 | Matsumoto |
| 2010/0179418 A1 | 7/2010 | Mueller et al. |
| 2010/0217117 A1 | 8/2010 | Glossop et al. |
| 2010/0249506 A1 | 9/2010 | Prisco |
| 2010/0317965 A1 | 12/2010 | Itkowitz et al. |
| 2011/0234780 A1* | 9/2011 | Ito ........................ A61B 1/05 348/E7.085 |
| 2011/0319815 A1 | 12/2011 | Roelle et al. |
| 2012/0065481 A1 | 3/2012 | Hunter et al. |
| 2012/0089022 A1 | 4/2012 | House et al. |
| 2012/0120091 A1 | 5/2012 | Koudijs et al. |
| 2012/0289843 A1 | 11/2012 | Chopra et al. |
| 2013/0179820 A1 | 7/2013 | Asami et al. |
| 2013/0204124 A1 | 8/2013 | Duindam |
| 2013/0281838 A1 | 10/2013 | Trumer et al. |
| 2013/0345719 A1 | 12/2013 | Donhowe et al. |
| 2014/0142422 A1 | 5/2014 | Manzke et al. |
| 2014/0188440 A1 | 7/2014 | Donhowe et al. |
| 2014/0211213 A1 | 7/2014 | Weiss |
| 2014/0350391 A1 | 11/2014 | Prisco et al. |
| 2015/0057498 A1* | 2/2015 | Akimoto ............ A61B 1/00043 600/103 |
| 2015/0073265 A1 | 3/2015 | Popovic et al. |
| 2016/0000302 A1 | 1/2016 | Brown et al. |
| 2016/0000517 A1 | 1/2016 | Kehat et al. |
| 2016/0005220 A1* | 1/2016 | Weingarten ............ A61B 34/10 382/131 |
| 2016/0070878 A1 | 3/2016 | Soper et al. |
| 2016/0073928 A1 | 3/2016 | Soper et al. |
| 2016/0183841 A1 | 6/2016 | Duindam et al. |
| 2016/0300017 A1 | 10/2016 | Lee et al. |
| 2016/0371883 A1 | 12/2016 | Merkine et al. |
| 2017/0071504 A1 | 3/2017 | Wang |
| 2017/0084027 A1 | 3/2017 | Mintz et al. |
| 2017/0151027 A1 | 6/2017 | Walker et al. |
| 2018/0177383 A1 | 6/2018 | Noonan et al. |
| 2020/0030044 A1 | 1/2020 | Wang et al. |
| 2020/0078103 A1 | 3/2020 | Duindam et al. |
| 2020/0129239 A1 | 4/2020 | Bianchi et al. |
| 2023/0200790 A1 | 6/2023 | Duindam et al. |

FOREIGN PATENT DOCUMENTS

| | | |
|---|---|---|
| CN | 105193503 A | 12/2015 |
| CN | 105636541 A | 6/2016 |
| CN | 106232001 A | 12/2016 |
| EP | 1103229 A2 | 5/2001 |
| EP | 2085017 A1 | 8/2009 |
| EP | 3478161 A1 | 5/2019 |
| JP | H08332191 A | 12/1996 |
| JP | 2004506466 A | 3/2004 |
| JP | 2004513684 A | 5/2004 |
| JP | 2008000261 A | 1/2008 |
| JP | 2015519987 A | 7/2015 |
| JP | 2016030125 A | 3/2016 |
| WO | WO-9729709 A1 | 8/1997 |
| WO | WO-0215775 A2 | 2/2002 |
| WO | WO-2007047782 A2 | 4/2007 |
| WO | WO-2008125910 A2 | 10/2008 |
| WO | WO-2009138871 A2 | 11/2009 |
| WO | WO-2011043982 A1 | 4/2011 |
| WO | WO-2014028394 A1 | 2/2014 |
| WO | WO-2014141968 A1 | 9/2014 |
| WO | WO-2015023665 A1 | 2/2015 |
| WO | WO-2015164587 A2 | 10/2015 |
| WO | WO-2016018646 A1 | 2/2016 |
| WO | WO-2016018648 A1 | 2/2016 |
| WO | WO-2016032846 A1 | 3/2016 |
| WO | WO-2016040080 A1 | 3/2016 |
| WO | WO-2018005680 A1 | 1/2018 |
| WO | WO-2018005842 A1 | 1/2018 |

OTHER PUBLICATIONS

International Search Report and Written Opinion for Application No. PCT/US2018/028190, dated Aug. 3, 2018, 14 pages.
Vertut, Jean and Phillipe Colffet, Robot Technology: Teleoperation and Robotics Evolution and Development, English translation, Prentice-Hall, Inc., Inglewood Cliffs, NJ, USA 1986, vol. 3A, 332 pages.
Office Action for Chinese Application No. CN20188030958, dated Aug. 24, 2022, 21 pages.
Office Action dated Apr. 8, 2021 for Chinese Application No. 201780039120 filed Jun. 29, 2017, 28 pages.
Extended European Search Report for Application No. EP18787852.5 dated Mar. 5, 2021, 14 pages.

(56) References Cited

OTHER PUBLICATIONS

Extended European Search Report for Application No. EP14836490. 4, dated Mar. 24, 2017, 9 pages.
Extended European Search Report for Application No. EP17821289 dated Feb. 7, 2020, 9 pages.
Extended European Search Report for Application No. EP17821278 dated Jan. 23, 2020, 12 pages.
International Preliminary Report on Patentability for Application No. PCT/US2014/050715, dated Feb. 25, 2016, 14 pages.
International Preliminary Report on Patentability for Application No. PCT/US2017/040095, dated Jan. 10, 2019, 8 pages.
International Search Report and Written Opinion for Application No. PCT/US2014/050715, dated Nov. 13, 2014, 17 pages.
International Search Report and Written Opinion for Application No. PCT/US2017/040067, dated Aug. 30, 2017, 13 pages.
International Search Report and Written Opinion for Application No. PCT/US2017/040095, dated Nov. 10, 2017, 11 pages.
Keller S.G., et al., "Equivalent Stress and Strain Distribution in Helical Compression Springs Subjected to Bending," The Journal of Strain Analysis for Engineering Design, Aug. 2011, vol. 46 (6), pp. 405-415.
Partial Supplementary European Search Report for Application No. EP18787852.5 dated Dec. 2, 2020, 17 pages.
Office Action for Chinese Application No. CN20188030958, dated Apr. 14, 2023, 27 pages.
Extended European Search Report for Application No. EP23182322. 0, dated Oct. 2, 2023, 11 pages.
Office Action for Chinese Application No. CN20188030958. dated Sep. 16, 2023. 18 pages.

* cited by examiner

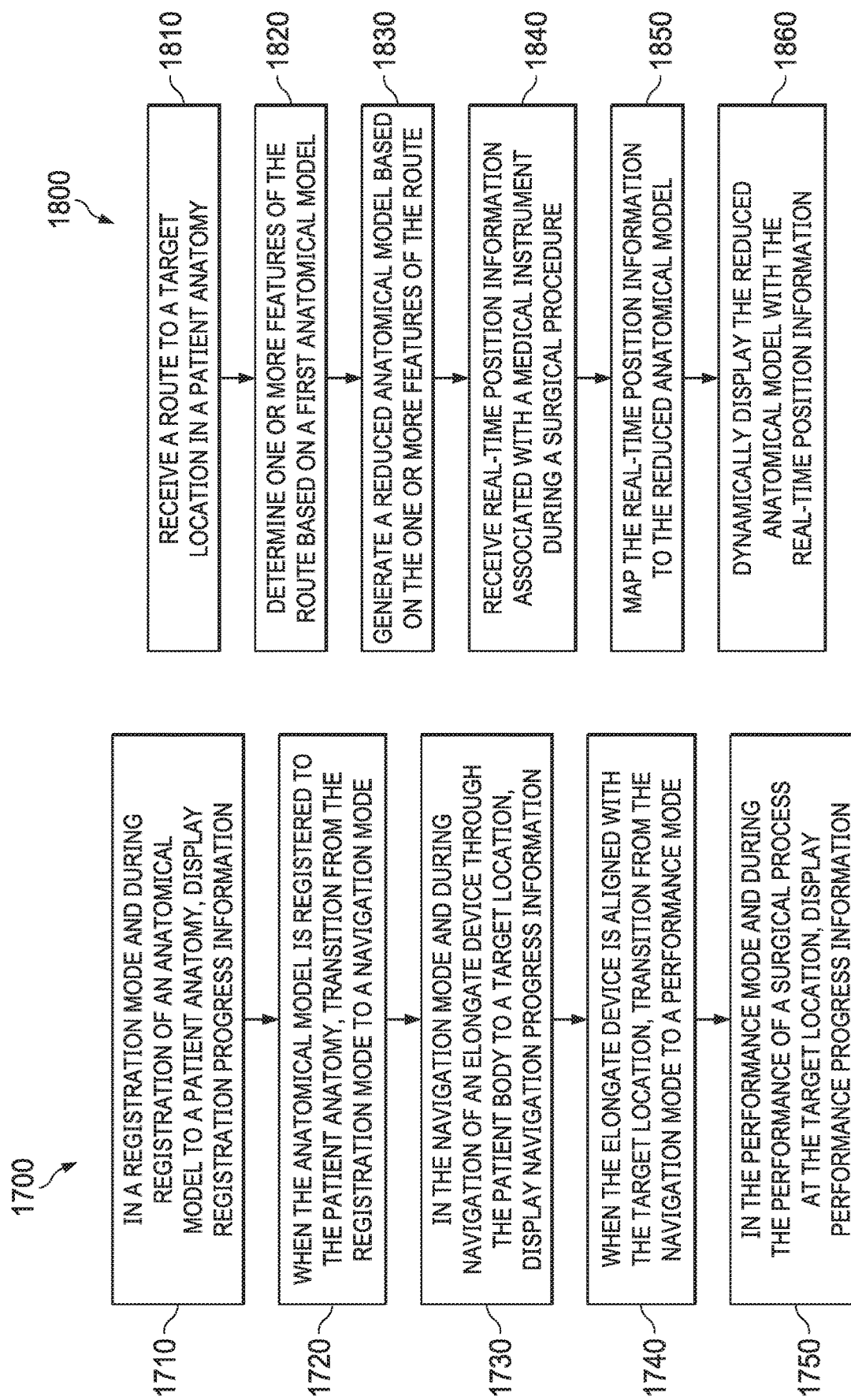

GRAPHICAL USER INTERFACE FOR MONITORING AN IMAGE-GUIDED PROCEDURE

RELATED APPLICATIONS

This patent application is a U.S. national phase of International Application No. PCT/US2018/028190, filed Apr. 18, 2018, which designated the U.S. and claims priority to and benefit of the filing date of U.S. Provisional Patent Application No. 62/486,879, filed Apr. 18, 2017, entitled "Graphical User Interface for Monitoring an Image-Guided Procedure," which are hereby incorporated by reference herein in their entirety.

TECHNICAL FIELD

The present disclosure is directed to systems and methods for performing a medical procedure and more particularly to systems and methods for monitoring an image-guided procedure using a graphical user interface.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel during an image-guided procedure involves the management of several degrees of freedom including at least the management of insertion and retraction of the elongate device as well as steering and/or bend radius of the device. In addition, different modes of operation may also be supported.

Accordingly, it would be advantageous to provide a graphical user interface that supports intuitive control and management of medical instruments including flexible and/or steerable elongate devices, such as steerable catheters, that are suitable for use during minimally invasive medical techniques.

SUMMARY

The embodiments of the invention are best summarized by the claims that follow the description.

According to some embodiments, a method for displaying an anatomy may include providing a graphical user interface, receiving a first anatomical representation including a 3D representation of a plurality of passageways in the anatomy and a route to a target location within the plurality of passageways, generating a reduced anatomical representation based on a subset of the plurality of passageways where the subset of the plurality of passageways includes path passageways directly connected to the route. and displaying the reduced anatomical representation as a linear anatomical representation. Implementations may include one or more of the following features: the method where the anatomy corresponds to lungs, and where the plurality of passageways in the anatomy correspond to airways of the lungs; the method where the target location includes one or more of a lesion, a nodule, and a tumor; the method where a width of the path passageways is indicated in the linear anatomical representation by vertically spaced lines having a tiered separation; the method where the tiered separation of the vertically spaced lines is tiered down for path passageways having a higher branching generation; the method where locations of branches off the path passageways are included in the linear anatomical representation; the method where the locations of the branches are includes clipped branches without a full branching structure of the branches; the method further including displaying an alternative route indicator representing an alternative route to the target location; the method further including displaying a target icon when one or more of the branches leads to a second target location; the method further including displaying an insertion trajectory from an end of the route to the target location; the method further including identifying a hazard associated with the route and displaying a location of the hazard relative to the insertion trajectory; the method where the hazard includes one or more of pleura, blood vessels, large bullae, and a heart; the method further including receiving real-time position information associated with an instrument during traversal of the route, mapping the real-time position information to the reduced anatomical representation, and dynamically displaying the real-time position information with the reduced anatomical representation; the method where dynamically displaying the real-time position information includes displaying one or more indicators when an anomaly is detected; the method where when the anomaly includes steering the instrument down an incorrect passageway, the one or more indicators includes a wrong turn indicator; the method where when the anomaly includes driving the instrument beyond an end of the route, the one or more indicators includes a reverse indicator; the method where when the anomaly includes a tight bend radius of the instrument, the one or more indicators includes an excessive bend indicator; the method where when the anomaly includes a tight bend radius of the instrument, an appearance of the instrument in the reduced anatomical model is modified.

According to some embodiments, a medical device may include an elongate device including a flexible body, a tracking system disposed along at least a portion of the flexible body, and one or more processors communicatively coupled to the tracking system. The one or more processors are configured to receive a route to a target location in an anatomy, determine one or more features of the route based on a first anatomical representation, generate a reduced anatomical representation based on the one or more features of the route, receive real-time position information from the tracking system, associate the real-time position information to the reduced anatomical representation, and dynamically display the reduced anatomical representation with the associated real-time position information. Implementations may include one or more of the following features: the medical device where the anatomy corresponds to lungs, and where the first anatomical representation includes a plurality of passageways in the anatomy that correspond to airways of the lungs; the medical device where the reduced anatomical representation is displayed as a linear anatomical representation; the medical device where the one or more features of the route include locations of branches along the route; the medical device where the locations of the branches in the reduced anatomical representation include clipped branches without a full branching structure of the branches; the medical device where an alternative route indicator is displayed to represent an alternative route to the target location; the medical device where a target icon is displayed when one or more of the branches leads to a second target location; the medical device where the one or more features of the route include an insertion trajectory from an end of the route to the target location; the medical device where the one or more features of the route include a hazard associated with the route; the medical device where dynamically displaying the real-time position information includes displaying one or more indicators when an anomaly is detected; the medical device where the one or more indicators includes one or more of a wrong turn indicator, a reverse indicator, and an excessive bend indicator.

According to some embodiments, a method for displaying a target within an anatomy may include providing a graphical user interface, receiving, via the graphical user interface, an anatomical representation, determining a target relative to the anatomical representation, determining an uncertainty zone associated with the target, and displaying the target relative to the anatomical representation, where the uncertainty zone is displayed as at least partially surrounding the target. Implementations may include one or more of the following features: the method where the anatomical representation is registered to an anatomy, and where the uncertainty zone is determined based on a registration uncertainty; the method where the uncertainty zone is determined based on a predetermined size of the target; the method where the uncertainty zone is determined based on an accessibility of the target; the method further including determining a location of a potential hazard; the method where the location of the potential hazard is relative to a position of the target; the method where the potential hazard is displayed relative to the target; the method where the potential hazard includes one or more of pleura, blood vessels, and large bullae within a patient lung.

According to some embodiments, a system may include a display system, a user input device, and one or more processors configured to perform operations. The operations may include receive an anatomical representation, receive a user input via the user input device associated with a target relative to the anatomical representation, determine an uncertainty zone associated with the target, and display the target relative to the anatomical representation via the display system, where the uncertainty zone is displayed as at least partially surrounding the target. Implementations may include one or more of the following features: the system where the anatomical model is registered to an anatomy, and where the uncertainty zone is determined based on a registration uncertainty; the system where the uncertainty zone is determined based on a predetermined size of the target. The system where the uncertainty zone is determined based on an accessibility of the target; the system further including determining a location of a potential hazard; the system where the location of the potential hazard is relative to a position of the target; the system where the potential hazard is displayed relative to the target; the system where the potential hazard includes one or more of blood vessels, large bullae and pleura within a patient lung.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIG. 17 is a simplified diagram of a method for monitoring a medical procedure according to some embodiments.

FIG. 18 is a simplified diagram of a method for monitoring a medical procedure using a graphical user interface according to some embodiments.

Figure 1:
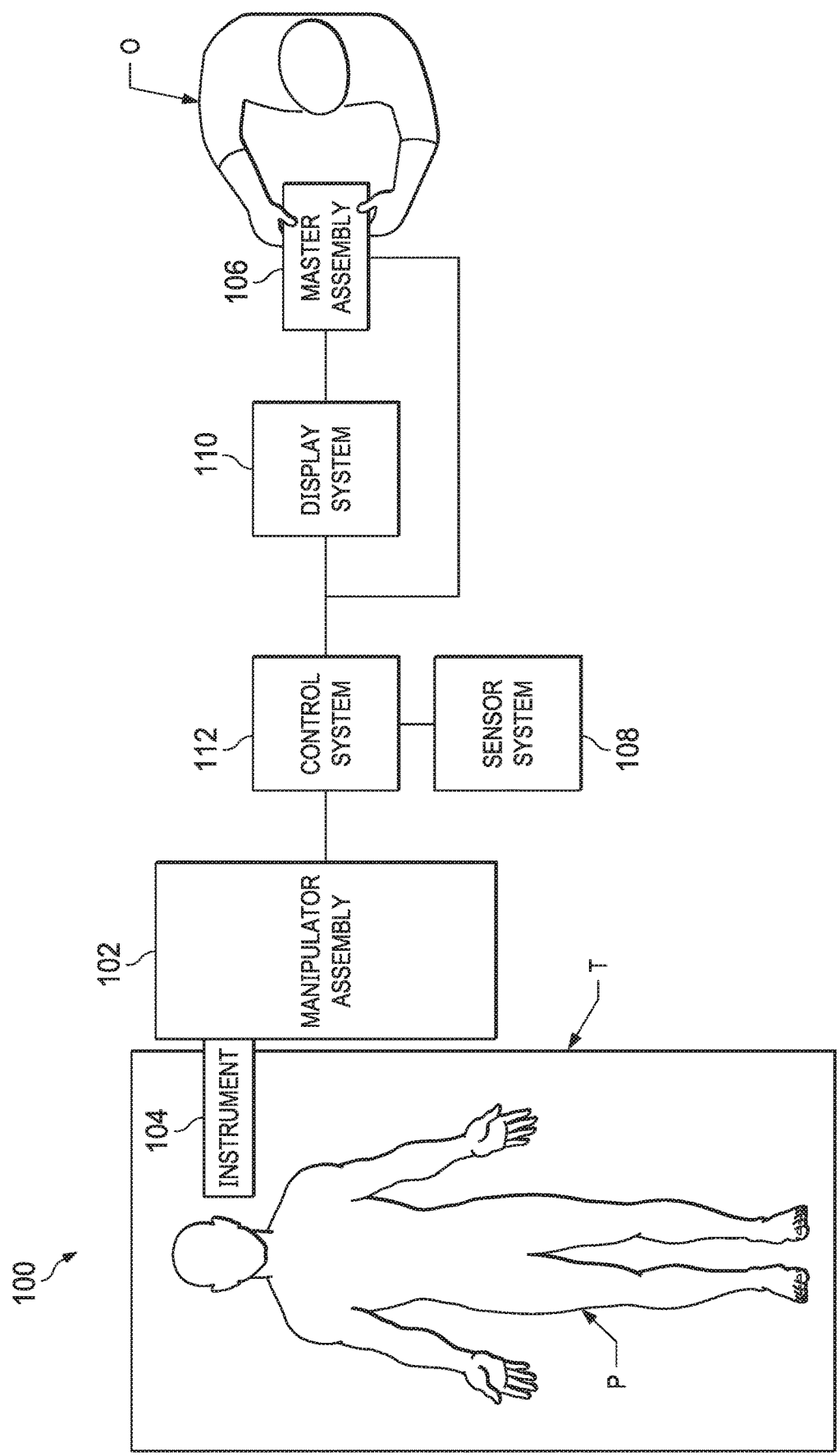
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a surgeon's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MM), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from representations (e.g., models) created from the pre-operative or intra-operative image data sets.

In some embodiments, often for purposes of imaged guided medical procedures, display system 110 may display a virtual navigational image in which the actual location of medical instrument 104 is registered (i.e., dynamically referenced) with the preoperative or concurrent images from a representation (e.g., a model). This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered representation (e.g., a model), such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided medical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the medical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figures 2A, 2B:
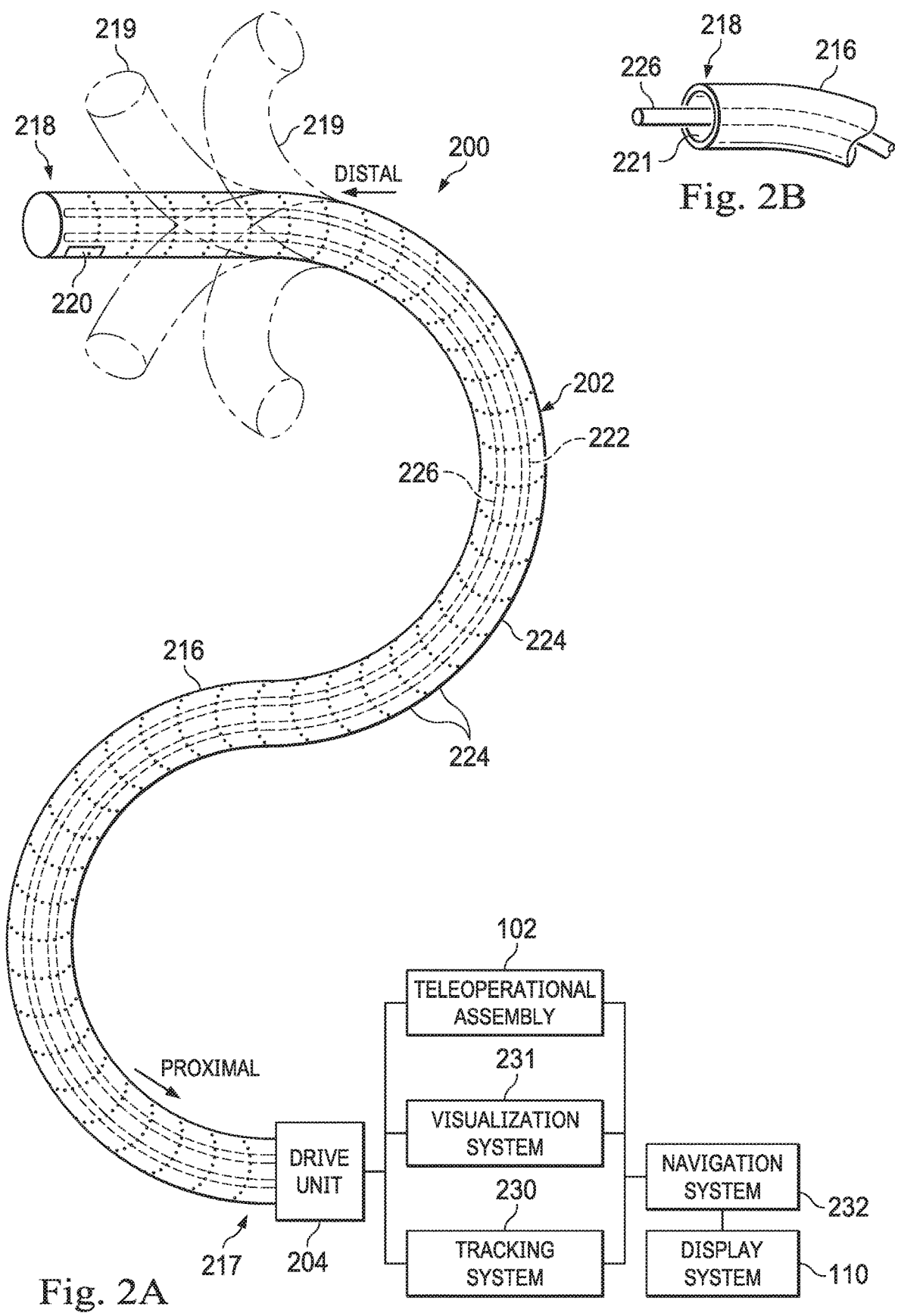
FIG. 2A is a simplified diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202 coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of flexible body 216 at distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of flexible body 216 may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained representations (e.g., models) to provide the physician, clinician, or surgeon or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
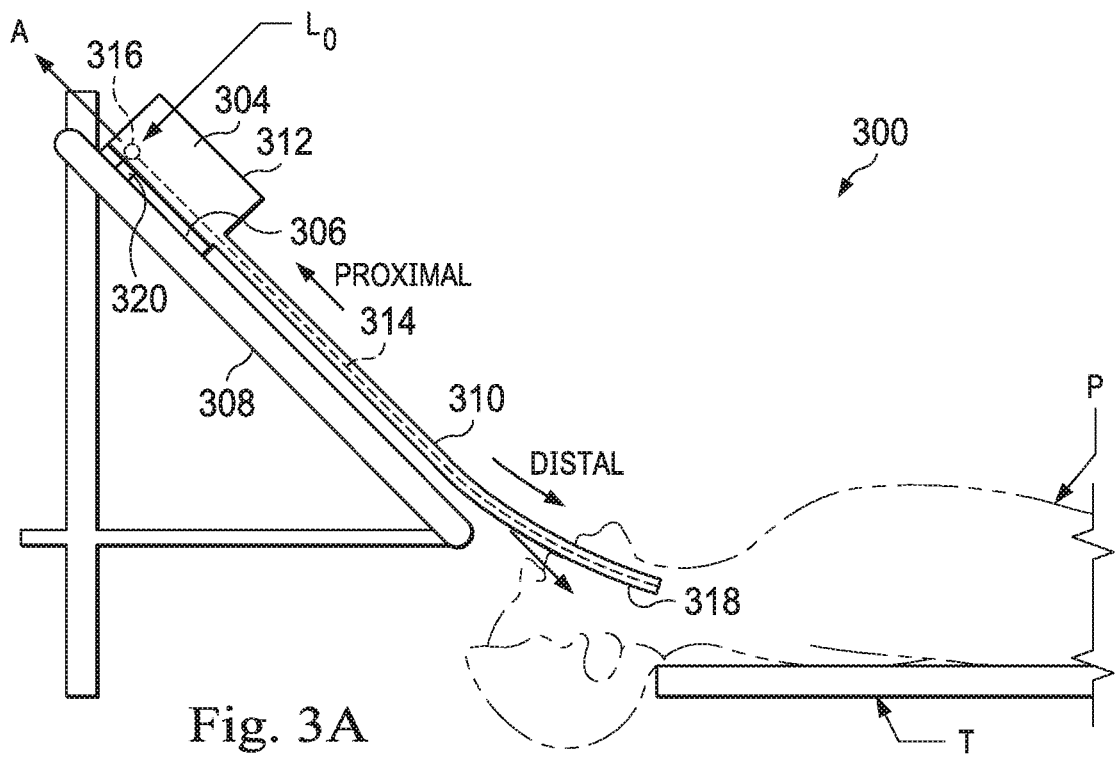
FIGS. 3A and 3B are simplified diagrams of side views of a patient coordinate space including a medical instrument mounted on an insertion assembly according to some embodiments.
Figure 3B:
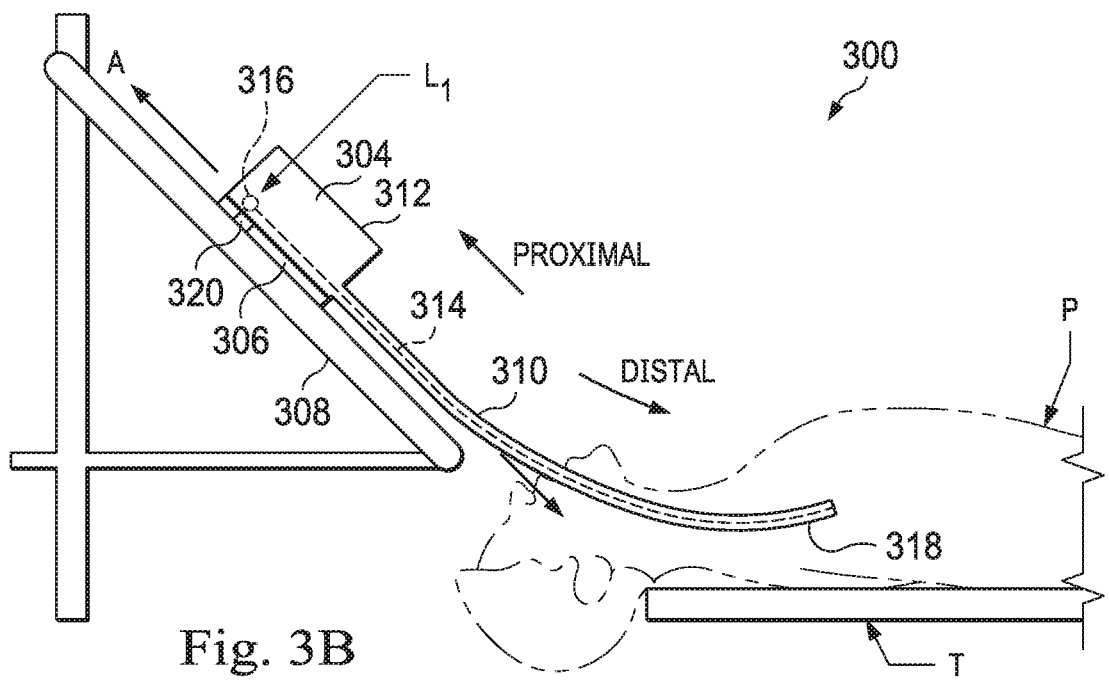

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position LX may further be used as an indicator of the distance or insertion depth to which distal end 318 of elongate device 310 is inserted into the passageways of the anatomy of patient P.

In an illustrative application, a medical instrument system, such as medical instrument system 200, may include a robotic catheter system for use in lung biopsy procedures. A catheter of the robotic catheter system provides a conduit for tools such as endoscopes, endobronchial ultrasound (EBUS) probes, therapeutic tools, and/or biopsy tools to be delivered to locations within the airways where one or more targets of the lung biopsy, such as lesions, nodules, tumors, and/or the like, are present. When the catheter is driven through anatomy, typically an endoscope is installed such that a clinician, such as surgeon O, can monitor a live camera feed of a distal end of the catheter. The live camera feed and/or other real-time navigation information may be displayed to the clinician via a graphical user interface.

Before a biopsy procedure is performed using the robotic catheter system, pre-operative planning steps may be performed to plan the biopsy procedure. Pre-operative planning steps may include segmentation of a patient CT scan to create a three dimensional (3D) representation (e.g., a 3D model) of anatomy, selecting targets within the 3D model, determining airways in the model, growing the airways to form a connected tree of airways, and planning a path to the targets through the connected tree. One or more of these steps may be performed on the same robotic catheter system used to perform the biopsy, on a different medical instrument system, on a standalone processor, such as a workstation dedicated to pre-operative planning, and/or the like. The plan for the biopsy procedure may be saved (e.g., as one or more digital files) and transferred to the robotic catheter system used to perform the biopsy procedure. The saved plan may include the 3D model, identification of airways, target locations, paths to target locations, and/or the like. An example of a graphical user interface supporting the pre-operative planning steps is covered in concurrently filed U.S. Provisional Patent Application 62/486,896, filed Apr. 18, 2017, which is incorporated by reference above.

When the plan is transferred to the robotic catheter system, the 3D model of the anatomy is registered to the actual patient anatomy and/or the catheter within the patient anatomy. Consequently, the real-time position and orientation of the catheter may be projected onto the 3D model and displayed via the graphical user interface. The clinician can then proceed with driving the catheter through anatomy while monitoring navigation progress on the graphical user interface. For example, the clinician may drive the catheter along a predetermined path in the saved plan to navigate to the target location and/or perform a biopsy at a target location.

Illustrative embodiments of a graphical user interface for monitoring a medical procedure, including but not limited to the lung biopsy procedure described above, are provided below. The graphical user interface may include a registration mode that is used to monitor the registration of a 3D model to an anatomy, a navigation mode that is used to monitor the navigation of a medical instrument to a target location in the anatomy, and a performance mode that is used to monitor the performance of an interventional step at the target location. Some aspects of the graphical user interface are similar to features described in U.S. Provisional Patent Application No. 62/357,217, entitled "Graphical User Interface for Displaying Guidance Information During and Image-Guided Procedure" and filed Jun. 30, 2016, and U.S. Provisional Patent Application No. 62/357,258, entitled "Graphical User Interface for Displaying Guidance Information in a Plurality of Modes During and Image-Guided Procedure" and filed Jun. 30, 2017, which are hereby incorporated by reference in their entirety.

Figure 4:
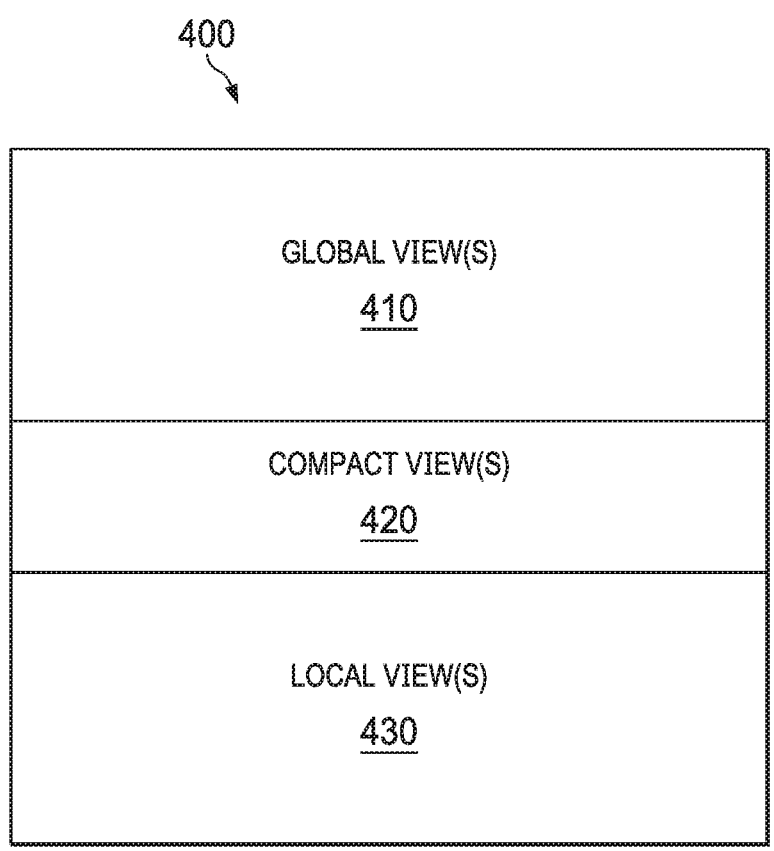
FIG. 4 is a simplified diagram of a graphical user interface displayable on a display system according to some embodiments

FIG. 4 is a simplified diagram of a graphical user interface 400 displayable on a display system, such as display system 110, according to some embodiments. Graphical user interface 400 displays information associated with a medical procedure in one or more views that are viewable to a clinician, such as surgeon O. Although an illustrative arrangement of views is depicted in FIG. 4, it is to be understood that graphical user interface 400 may display any suitable number of views, in any suitable arrangement, and/or on any suitable number of screens. In some examples, the number of concurrently displayed views may be varied by opening and closing views, minimizing and maximizing views, moving views between a foreground and background of graphical user interface 400, switching between screens, and/or otherwise fully or partially obscuring views. Similarly, the arrangement of the views—including their size, shape, orientation, ordering (in a case of overlapping views), and/or the like—may vary and/or may be user-configurable.

In some examples, the views displayed graphical user interface 400 may be arranged in an organized scheme to facilitate rapid access to relevant information. Although FIG. 4 depicts an illustrative example of one such organization scheme, many other organization schemes are possible. As depicted in FIG. 4, graphical user interface 400 includes an upper portion that displays one or more global views 410, a middle portion that displays one or more compact views 420, and a lower portion that displays one or more local views 430. Global views 410 generally display global aspects of the medical procedure to provide the clinician with a detailed picture of the current state of the medical procedure. Compact views 420 generally display a reduced set of information about the medical procedure in a simplified, uncluttered format to facilitate rapid comprehension by the clinician. Local views 430 generally display local aspects of the medical procedure to monitor movements and/or interventional steps performed by the medical instrument in real-time. Examples of global, compact, and local views 410-430 are discussed in greater detail below with reference to FIGS. 5A-5D.

In some examples, global, compact, and local views 410-430 may be arranged in various configurations other than those depicted in FIG. 4. For example, graphical user interface 400 may have a landscape layout in which global views 410 are positioned on the left, compact views 420 are oriented vertically in the middle, and local views 430 are positioned on the right. In some examples, global, compact, and local views 410-430 may be spread throughout graphical user interface 400, such that graphical user interface 400 may not be divisible into dedicated regions as depicted in FIG. 4. In some examples, graphical user interface 400 may include various views, controls, indicators, and/or the like, in addition to those depicted in FIG. 4. For example, graphical user interface 400 may include a header, footer, one or more sidebars, message bars, popup windows, backgrounds, overlays, and/or the like.

Graphical user interface 400 may be operated in different modes at various stages of the medical procedure. In some examples, the organization scheme may vary based on the mode of graphical user interface 400. In each mode, the arrangement of views may be selected to convey information that is available and/or relevant at the current stage of the medical procedure. In some examples, the modes may include a registration mode, a navigation mode, and/or a performance mode as discussed below. In some examples, various modes may overlap with each other and/or transition seamlessly between each other so as to behave as a single mode. For example, the navigation and performance modes may be seamlessly transitioned such that they may be considered a single hybrid navigation and performance mode.

FIGS. 5A-5D are simplified diagrams of a graphical user interface 500 in a plurality of modes according to some embodiments. According to some embodiments consistent with FIG. 4, graphical user interface 500 may correspond to graphical user interface 400. Accordingly, graphical user interface 500 displays information associated with a medical procedure in one or more views that are viewable to a clinician, such as surgeon O. In some examples, graphical user interface 500 and/or select windows or views within global views 510, compact views 520, and local views 530 may be displayed on an I/O device, such as a touchscreen, to receive user inputs for controlling and/or configuring graphical user interface 500. For example, the user inputs may allow the clinician to control the arrangement, zoom, perspective, rotation, color scheme, and/or other aspects of the configuration and/or appearance of graphical user interface 500. In some examples, user inputs may be received via a separate input device, such as a standalone control console. In some examples, a user input device may be omitted, such as when graphical user interface 500 is not configurable by the user.

Figure 5A:
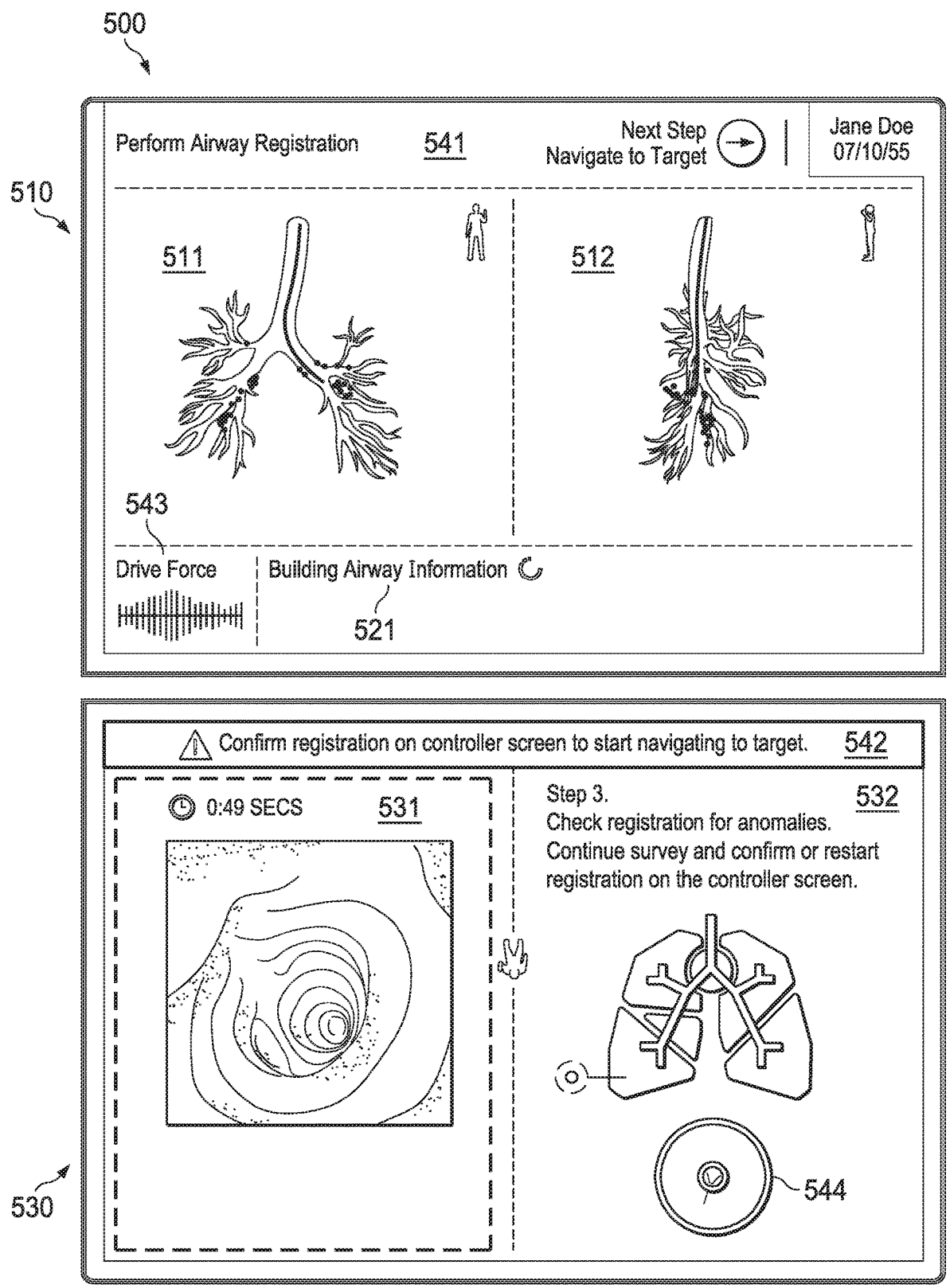
FIGS. 5A-5D are simplified diagrams of a graphical user interface in a plurality of modes according to some embodiments.

FIG. 5A illustrates graphical user interface 500 in a registration mode. The registration mode is used to monitor and aid in the registration of a 3D model to the anatomy at the start of the medical procedure. In an exemplary registration process, the clinician drives an instrument, such as a catheter with a localization sensor (e.g., a shape sensor, electromagnetic (EM) sensor, and/.or the like), to various portions of anatomy to collect registration data. For example, when the anatomy corresponds to lung, the clinician may drive the catheter to portions of the lung corresponding to the right middle lobe, left middle lobe, main stem bronchi, and/or the like. The localization sensor, such as shape sensor 222, is used to determine a series of points defining a position and orientation of the catheter in a sensor reference frame as the catheter is driven to the various portions of the anatomy. The series of points may additional or alternately be referenced to a robot sensor frame, e.g., using insertion, elevation, and/or setup joint axis encoder positions. The series of points forms a point cloud which is registered to the 3D model using a registration technique, such as the iterative closest point (ICP) algorithm and/or other similar algorithms. In some embodiments, guidance information may be provided to the clinician regarding where to drive the catheter in order to accelerate and/or improve the accuracy of the registration.

Accordingly, graphical user interface 500 in the registration mode may show one or more views that facilitate monitoring of the registration process. In some examples, graphical user interface 500 may display one or more global views 510 corresponding to global views 410. As depicted in FIG. 5A, global views 510 in the registration mode include a pair of dynamic point cloud views 511 and 512 from a front perspective and a side perspective, respectively. It is to be understood that other perspectives may be used, including user configurable perspectives and/or perspectives that are adjustable in real-time by the clinician (e.g., using controls to adjust zoom, rotation, appearance, and/or the like). Dynamic point cloud views 511 and 512 display three dimensional representations of the point cloud and are continuously updated as more points are added to the point cloud. In some examples, the three dimensional representations of the point cloud may be rendered in dynamic point cloud views 511 and 512 when the point cloud includes a sufficient amount of data to register the representation to the anatomy with reasonable accuracy. Examples of dynamic point cloud views are discussed in greater detail below with respect to FIGS. 6A-6B.

In some examples, graphical user interface 500 in the registration mode may not display compact views that correspond to compact views 420. In particular, one or more portions of compact views 420 may not be available until registration is complete. Instead, graphical user interface 500 in the registration mode may display status information 521. As depicted in FIG. 5A, status information 521 includes a message "Building Airway Information" and a waiting icon.

In some examples, graphical user interface 500 in the registration mode may display one or more local views 530 corresponding to local views 410. As depicted in FIG. 5A, local views 530 include a live camera feed 531 and a dynamic registration guidance view 532. Live camera feed 531 displays real-time images received from an endoscope positioned at a distal end of the medical instrument. Examples of dynamic registration guidance views are discussed in further detail below with reference to FIGS. 7A-7B. Examples of live camera feeds are discussed in further detail below with reference to FIGS. 12A-12B.

As depicted in FIG. 5A, graphical user interface 500 further includes a header 541 and a message bar 542. Header 541 displays a title (e.g., "Perform Airway Registration") and patient information. In some examples, header 541 may include a mode transition button to transition among the modes of graphical user interface 500. Message bar 542 displays one or more messages which may be used to inform the clinician of the next steps in the procedure (e.g., "Confirm registration on controller screen to start navigating to target"), send the clinician a reminder (e.g., "Use the breath hold timer during registration."), alert the clinician of a hazard, and/or the like. In some embodiments, the appearance of message bar 542 (e.g., color, size, texture, font, etc.) may change depending on the type of message. For example, an alert message may be displayed in red. Message bar 542 may be hidden when there is no message to display.

In some examples, graphical user interface 500 may include a drive force indicator 543 and a bend indicator 544. In some embodiments, bend indicator 544 may be used to warn the clinician when the catheter is positioned in anatomy such that one or more segments of the catheter is bent at a radius too tight for a tool, such as a biopsy needle, to pass through the catheter. For example, bend indicator 544 may appear when a tight bend radius is detected in the catheter (e.g., when the bend radius is below a predetermined threshold) and may be hidden otherwise. In some embodiments, bend indicator 544 may be displayed in ordinary conditions as an indication of the current shape of the tip of the catheter to improve user awareness of the configuration of the distal end. In this regard, the shape of bend indicator 544 may be computed from the actual measured shape of the catheter and/or may be an abstract iconic indicator. Examples of drive force indicators and bend indicators are discussed in greater detail below with reference to FIGS. 8 and 9, respectively.

When registration is complete, graphical user interface 500 transitions from the registration mode to the navigation mode. In some examples, graphical user interface 500 may automatically transition from the registration mode to the navigation mode in response to detecting that registration is complete. In some examples, the transition may be performed manually, such as in response to the clinician clicking a button in graphical user interface 500 (e.g., a mode transition button in header 541), activating an input on a separate input device (e.g., a touchscreen of a control console), and/or the like to proceed to the navigation mode.

Figure 5B:
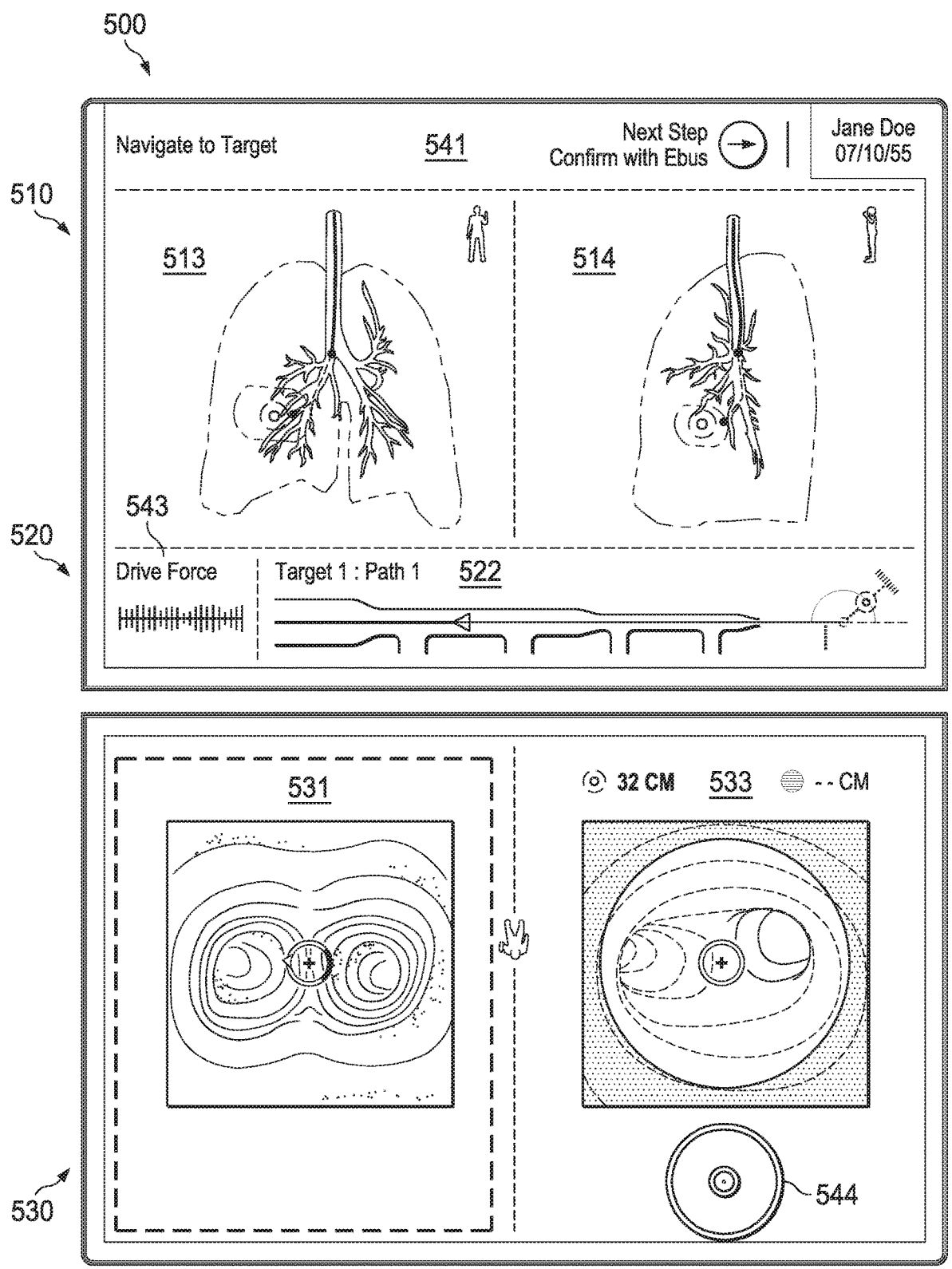

FIG. 5B illustrates graphical user interface 500 in the navigation mode according to some embodiments. In some examples, the navigation mode may be used to monitor and aid in the navigation of the catheter to the target location. For example, the navigation mode may be used when the clinician is driving the catheter along a route selected during the planning of the medical procedure. The navigation mode can further include indicators to the clinician providing directional guidance to the target along the route.

In the example depicted in FIG. 5B, global views 510 in the navigation mode include a pair of global anatomical models 513 and 514 from a front perspective and a side perspective, respectively. In another example, the perspective of global anatomical models 513 and/or 514 can be rotated by the clinician using an input device such as a scroll wheel, mouse or touchscreen to drag global anatomical models 513 and/or 514 to a desired orientation. In some embodiments, the clinician may rotate one view (e.g., global anatomical model 513) and, in response, another view (e.g., global anatomical models 514) can automatically rotate to provide a respective orthogonally oriented view. Examples of global anatomical models are described in greater detail below with reference to FIG. 10. In some examples, graphical user interface 500 in the navigation mode may display one or more compact views 520 corresponding to compact views 420. As depicted in FIG. 5B, compact views 520 include a reduced anatomical model 522. Reduced anatomical model 522 displays an elongated representation of the planned route to the target location, with various features along the route, including the target location, shown in a simplified format. Examples of reduced anatomical models are described in greater detail below with reference to FIGS. 11A-11C. Local views 530 in the navigation mode include live camera feed 531, similar to the registration mode. In some examples, supplemental guidance information may be superimposed on live camera feed 531 in the navigation mode, as discussed below with reference to FIGS. 12A-12B. Local views 530 may include a virtual distal view 533 that displays a rendering of the 3D model from the perspective of the distal end of the catheter. Examples of virtual distal views are discussed in further detail with reference to FIGS. 13A-13D.

Figure 5C:
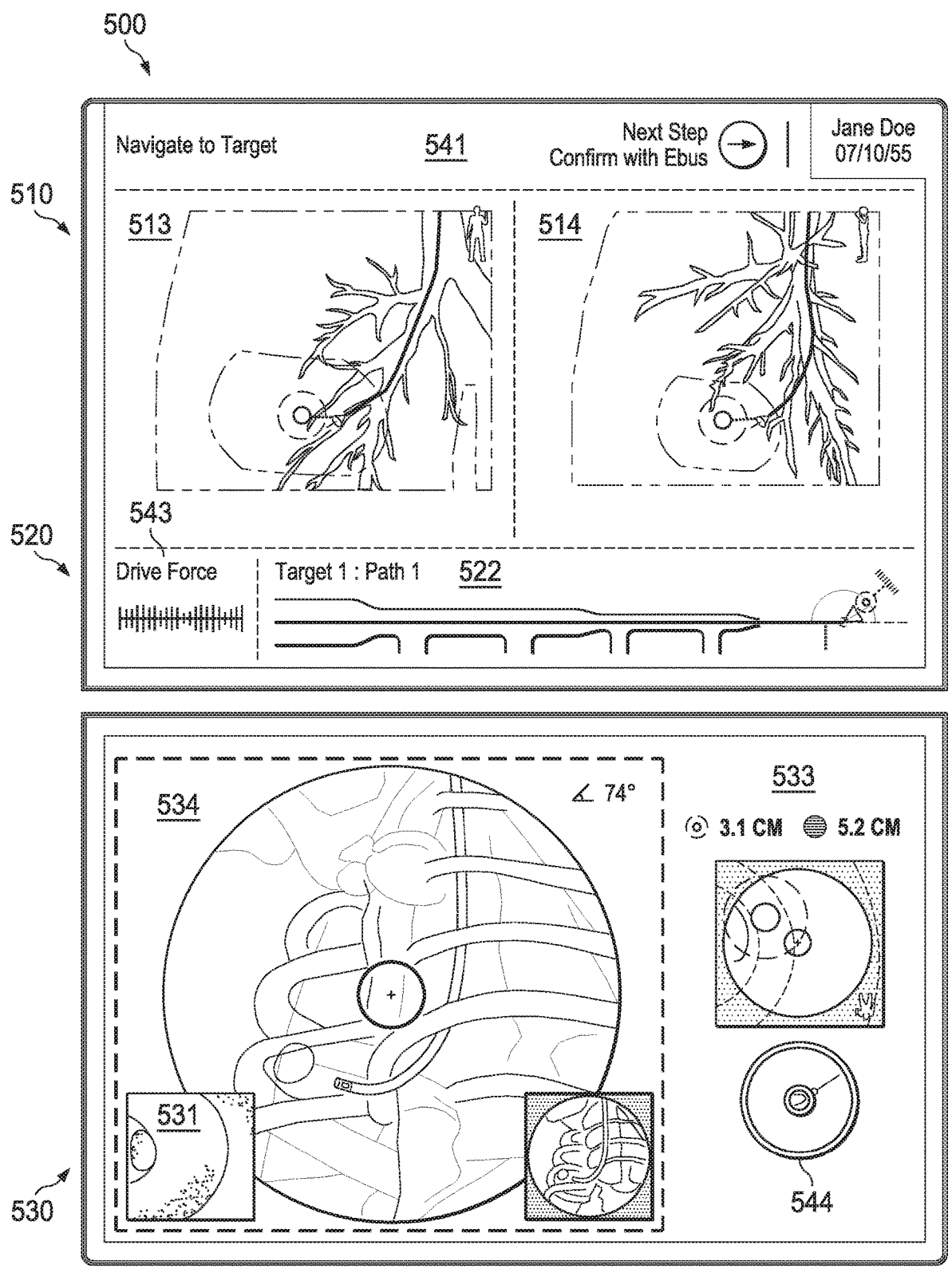

When a distal end of the catheter approaches the target location (e.g., when the distal end is within a specified range of the target location), an alternative configuration of graphical user interface 500 may be displayed, as depicted in FIG. 5C. In some examples, graphical user interface 500 may automatically transition from the configuration depicted in FIG. 5B to the alternative configuration depicted in FIG. 5C in response to detecting that the catheter is in proximity of the target location within a threshold and/or is aligned with the target location within a threshold. In some examples, the transition may be performed manually, such as in response to the clinician clicking a button in graphical user interface 500 and/or on a separate input device to proceed to the performance mode.

As depicted in FIG. 5C, global views 510 and compact views 520 are similar to FIG. 5B, although various adjustments to the displayed views may be made (e.g., displaying a zoomed in version of global views 510). However, various configurations of local views 530 may be displayed to assist the clinician with aligning the catheter to the target location when the catheter is in the proximity of the target location. For example, in place of and/or in addition to the live endoscopic view, a remote image view 534, such as a live fluoroscopic view, may be displayed, as will be described in more detail below. To accommodate remote image view 534, live endoscopic view 531 may be resized and/or relocated, e.g., to a lower left corner of the display. In some examples, the appearance of virtual distal view 533 may be altered to assist the clinician in identifying and aligning to the target location, including displaying semi-transparent passageway walls, a target indicator, an uncertainty zone, and/or a cross hair indicator.

When the clinician is ready to perform an interventional step at the target location, graphical user interface 500 transitions from the navigation mode to the performance mode. In some examples, graphical user interface 500 may automatically transition from the navigation mode to the performance mode in response to detecting that a camera probe is removed from the catheter (thereby eliminating the live endoscopic view) and/or a medical instrument for performing the interventional step is inserted into the catheter. In some examples, the transition may be performed manually, such as in response to the clinician clicking a button in graphical user interface 500 and/or on a separate input device.

Figure 5D:
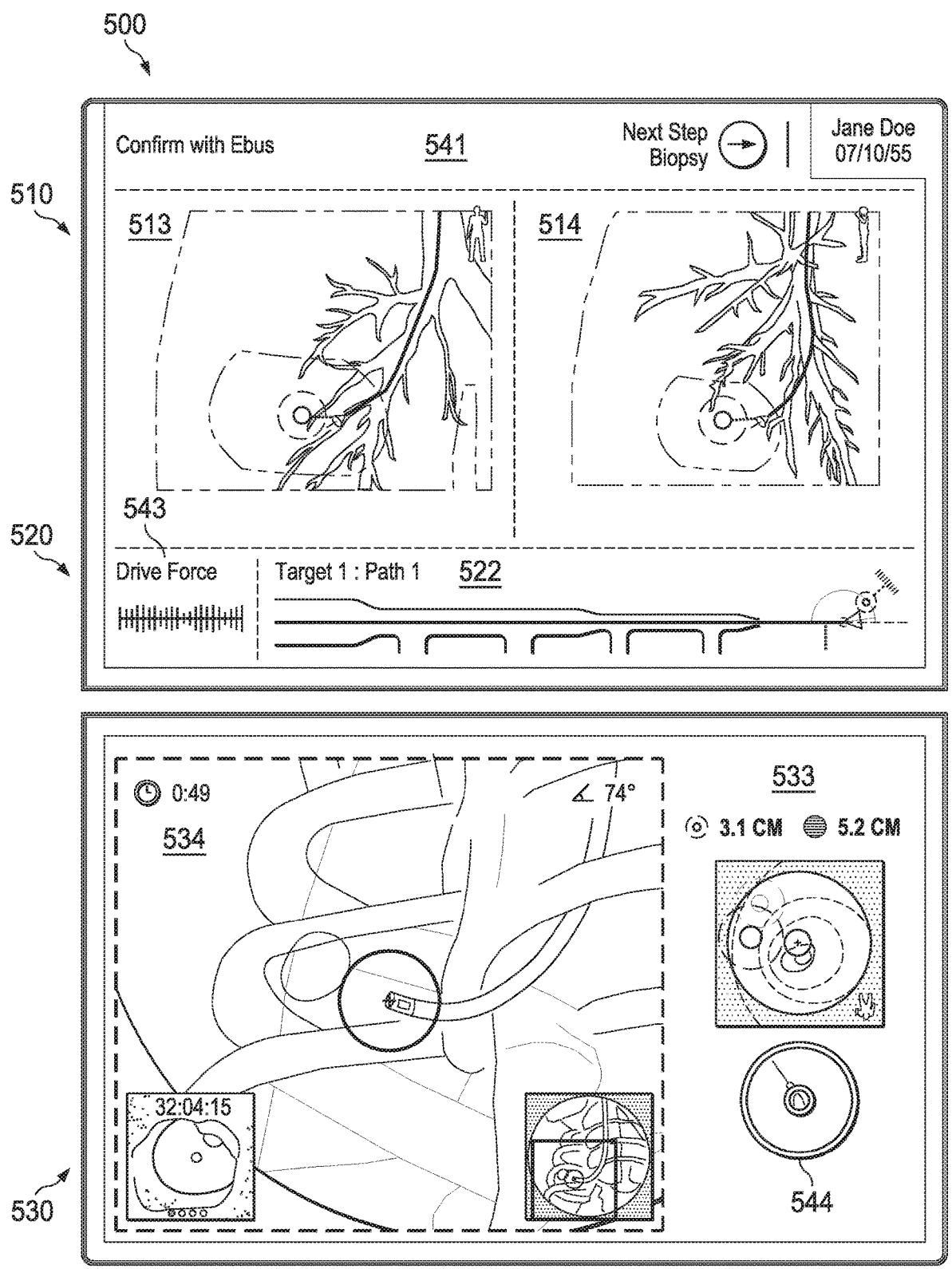

FIG. 5D illustrates graphical user interface 500 in a performance mode according to some embodiments. The performance mode is used to monitor the performance of an interventional step at the target location. For example, the interventional step may correspond to a biopsy, ablation, chemical delivery, physical manipulation of tissue, installation or removal of a biomedical device, and/or the like. In some embodiments, an endoscope that was inserted through the catheter to provide a live camera feed during the navigation process is removed during the performance of the interventional step and replaced with a tool used to perform the interventional step. When the endoscope is removed, the catheter remains parked near the target location to provide a conduit for the tool to reach the target location. In some embodiments, before, during, and/or after inserting the tool, a probe, such as an endo-bronchial ultrasound (EBUS) probe, may be inserted into the parked catheter after removing the endoscope. For example, a radial EBUS probe may be extended just beyond the distal tip of the catheter to provide a 360 degree ultrasound view. The clinician may use the ultrasound view to verify the position of the target location relative to the distal end of the catheter. For instance, in a scenario where the registration is inaccurate and/or the anatomy has shifted and/or deformed since registration was performed, the catheter may be misaligned with respect to the target location. In this regard, the ultrasound view may be used to reposition the catheter to better align with the target. Once the clinician is ready to perform the interventional step, the probe used for navigation and/or fine alignment (e.g., the endoscope or EBUS probe) may be withdrawn and replaced with a procedure-specific tool, such as a biopsy needle.

As depicted in FIG. 5D, global views 510 and compact views 520 in the performance mode are similar to the navigation mode, although various adjustments to the displayed views may be made (e.g., displaying a zoomed in version of global views 510 in the performance mode). Adjustments may be made manually by the clinician and/or automatically by the display system. As depicted in FIG. 5D, local views 530 in the performance mode include a remote image view 534. In this example, remote image view 534 includes a fluoroscopy image oriented to capture the anatomy in the vicinity of the distal end of the catheter. Examples of remote image views are discussed in further detail with reference to FIGS. 15A-15C. Other views included in local views 530 in the performance mode are generally similar to the navigation mode, although they may be resized and/or repositioned to accommodate remote image view 534.

Figure 6A:
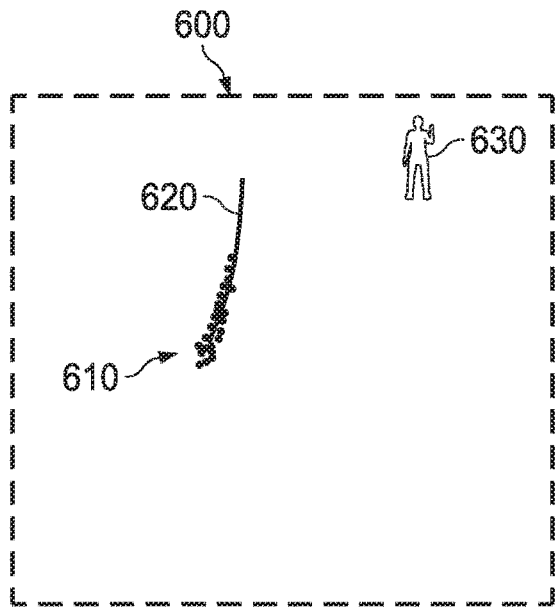
FIGS. 6A-6B are simplified diagrams of a dynamic point cloud view at two different times during a registration process according to some embodiments.
Figure 6B:
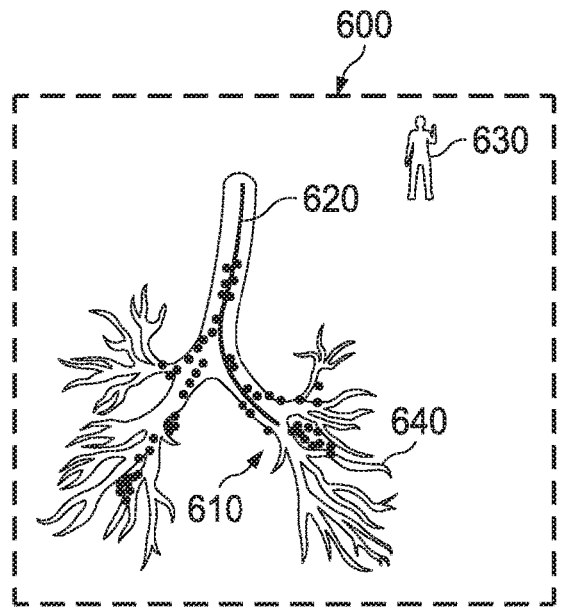

FIGS. 6A-6B are simplified diagrams of a dynamic point cloud view 600 at two different times during a registration process according to some embodiments. According to some embodiments consistent with FIG. 5A, dynamic point cloud view 600 may correspond to one or more of dynamic point cloud views 511 and/or 512 of graphical user interface 400. However, it is to be understood that dynamic point cloud view 600 may be displayed in contexts other than graphical user interface 500, including as a standalone graphical user interface component and/or in conjunction with views other than those depicted in graphical user interface 500.

Dynamic point cloud view 600 depicts a point cloud 610 corresponding to registration data captured using a position probe 620. As depicted in FIGS. 6A-6B, point cloud 610 is displayed using blue dots, and position probe 620 is displayed as a green line. An orientation icon 630 in the top right corner indicates the orientation of the plot relative to the anatomy. FIG. 6A depicts dynamic point cloud view 600 early in the registration process, when point cloud 610 corresponds to registration data captured along a single, unbranched path within the anatomy. In some examples, a single unbranched path within the anatomy may be insufficient to perform registration with reasonable accuracy. Accordingly, no 3D model is rendered in FIG. 6A.

FIG. 6B depicts dynamic point cloud view 600 later in the registration process, when point cloud 610 has grown to span multiple branches (e.g., multiple airways) and/or multiple partitions (e.g., multiple lobes of the lungs). When point cloud 610 includes a sufficient amount of registration data to perform registration, an estimated position of a model 630 relative to point cloud 610 is calculated using a registration algorithm such as ICP. Once the estimated position is calculated, a model 630 may be rendered in dynamic point cloud view 600. As depicted FIG. 6B, model 630 is displayed in translucent gray. As the point cloud continues to grow, the estimated position of model 630 may be continuously updated. The color and/or translucency of model 630 may also be adjusted in response to the level of completion of the registration process, e.g. the model may become more opaque as the registration quality improves and/or as the point cloud coverage of the model increases.

A clinician may visually assess the accuracy of the registration by identifying anomalies in dynamic point cloud view 600. For example, in FIG. 6B, when portions of point cloud 610 and/or position probe 610 are not positioned inside of model 630, the clinician may determine that the registration is inaccurate because point cloud 610 and position probe 620 are generally expected to fall within the boundaries of model 630. In a scenario where the registration accuracy is unsatisfactory to the clinician, the clinician may continue to capture additional points to try to improve the registration accuracy, may restart the registration process, and/or may opt to proceed to the next stage of the procedure.

Figure 7A:
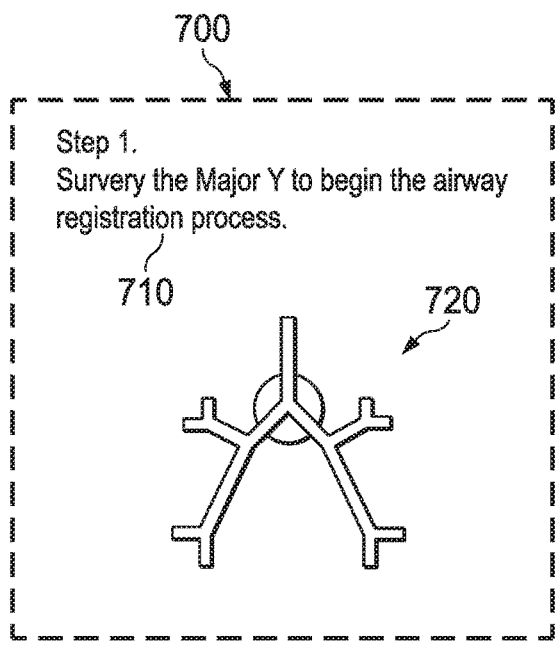
FIGS. 7A-7B are simplified diagrams of a dynamic registration guidance view at two different times according to some embodiments.
Figure 7B:
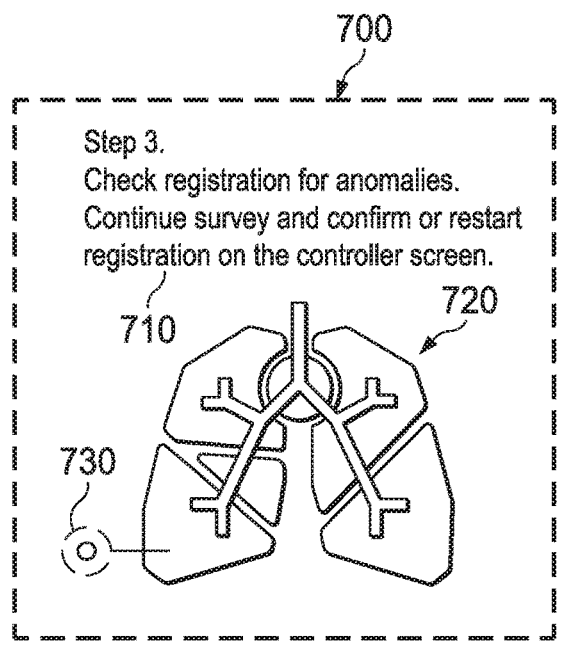

FIGS. 7A-7B are simplified diagrams of a dynamic registration guidance view 700 at two different times according to some embodiments. According to some embodiments consistent with FIG. 5A, dynamic registration guidance view 700 may correspond to dynamic registration guidance view 532. However, it is to be understood that dynamic registration guidance view 700 may be displayed in contexts other than graphical user interface 500, including as a standalone view and/or in conjunction with views other than those depicted in graphical user interface 500.

Dynamic registration guidance view 700 displays information and/or instructions that are dynamically updated to reflect registration progress. In some examples, dynamic registration guidance view 700 may include written instructions 710 describing the current step in the registration process and/or providing suggested areas in the anatomy where additional points should be gathered. When the current step is complete, the content of instructions 710 may be automatically updated to describe the next step in the registration process.

In some examples, dynamic registration guidance view 700 may include a schematic representation 720 of the anatomy. Each segment of schematic representation 720 corresponds to a portion of the anatomy. As depicted in FIGS. 7A-7B, the segments include various lobes of the lung, major airways (e.g., main stem bronchi), and the area around the main carina of the lung. When a sufficient amount of registration data has been acquired from a particular segment of the anatomy, one or more attributes of the segment (e.g., color, shape, size, texture, text label, and/or the like) may be updated to indicate that registration is complete with respect to that portion of the anatomy. For example, a segment may transition from unfilled (e.g., no color) to filled (e.g., solid color) when a threshold amount of registration data is collected from the segment. Additionally or alternately, the appearance of the segment may gradually transition as more registration data is collected from the segment. In some examples, one or more segments with the least amount of registration data may be identified. By monitoring the changes in the appearance of the segments in schematic representation 720, the clinician is notified when registration is complete with respect to each segment and may take steps to move the position probe to portions of the anatomy that do not yet have a sufficient amount of registration data. Consequently, the registration process may be accelerated because the clinician is instructed to grow the registration point cloud in regions where the registration data is sparsest and/or otherwise not yet sufficient to perform accurate registration.

FIG. 7A depicts schematic representation 720 early in the registration process, before sufficient registration data has been captured from any segment. Accordingly, none of the segments are filled in. By contrast, FIG. 7B depicts schematic representation 720 later in the registration process after sufficient registration data has been captured from all segments. Accordingly, each segment of schematic representation 720 is colored solid blue. A target indicator 730 appears in FIG. 7B to indicate which segment includes the target location of the medical procedure. Multiple target indicators may appear when the medical procedure includes more than one target location. In an alternative example, the target indicator/s could be overlaid on the segment, and/or the location of the target may be indicated by altering the color, weight, hue, and/or transparency of the corresponding segment.

Figure 8:
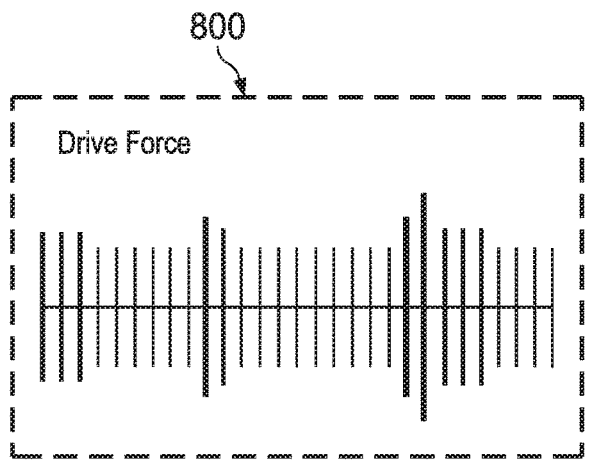
FIG. 8 is a simplified diagram of a drive force indicator according to some embodiments.

FIG. 8 is a simplified diagram of a drive force indicator 800 according to some embodiments. According to some embodiments consistent with FIGS. 5A-5D, drive force indicator 800 may correspond to drive force indicator 543. However, it is to be understood that drive force indicator 800 may be displayed in contexts other than graphical user interface 500, including as a standalone view and/or in conjunction with views other than those depicted in graphical user interface 500.

Drive force indicator 800 displays a visual and/or an alphanumeric representation of the axial drive force applied to the catheter during operation (e.g., during insertion and/or withdrawal of the catheter from the patient anatomy). For example, a large drive force may be applied when the catheter is being inserted into passageway that is narrower than the catheter diameter, and/or when the catheter is otherwise impeded by an obstruction. Many techniques for monitoring the applied drive force are possible. As depicted in FIG. 8, the drive force is plotted as a function of time using a symmetric bar plot. The most recent drive force measurement is on the right, and historical measurements are plotted on the left. In some embodiments, various other plotting techniques may be used, such as a one-sided bar plot, a line plot, a scatter plot, and/or the like. Alternately or additional, the current drive force may be displayed using a meter, alphanumeric text, and/or the like. In some examples, the appearance of drive force indicator 800 (e.g., color, texture, size, and/or the like) may vary as a function of drive force and/or time. As depicted in FIG. 8, the color of the bars varies among gray, yellow, or red based on the magnitude of the drive force, and the thickness of the bars is gradually reduced further back in time. In some examples, drive force indicator 800 may be positioned adjacent to and/or within a view that depicts a representation of the catheter, such as reduced anatomical view 522. In this arrangement, drive force indicator 800 may convey a visual impression of pushing the catheter into the anatomy. Various examples of drive force indicators are further described in U.S. Provisional Patent Application No. 62/357,258, which is incorporated by reference above.

Figure 9:
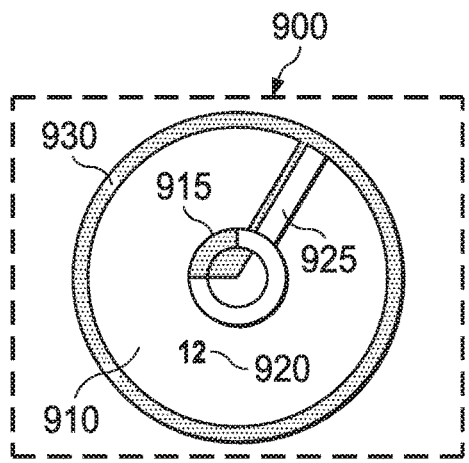
FIG. 9 is a simplified diagram of a bend indicator according to some embodiments.

FIG. 9 is a simplified diagram of a bend indicator 900 according to some embodiments. According to some embodiments consistent with FIGS. 5A-5D, bend indicator 900 may correspond to bend indicator 544. However, it is to be understood that bend indicator 900 may be displayed in contexts other than graphical user interface 500, including as a standalone view and/or in conjunction with views other than those depicted in graphical user interface 500. As discussed previously, bend indicator 900 may appear when a tight bend radius is detected in the catheter (e.g., when the bend radius is below a predetermined threshold) and may be hidden otherwise. Alternatively, selected portions of bend indicator 900 may be hidden when no tight bend is present, e.g. numerical bend radius 910.

Bend indicator 900 provides a schematic bend representation 910 of the catheter. When the distal tip of the catheter is bent, a bend line 925 appears which indicates the direction the catheter distal end is bending. For example, as depicted in FIG. 9, the bend line 925 appears on the upper right of a ring 915, indicating that the catheter is bent to the right. Thus to straighten the catheter, the catheter may be steered to the lower left to reduce the bend. In some examples, when the catheter distal end is straight, bend line 925 may be hidden.

In some examples, schematic bend representation 910 may include a rendering of a distal end of the catheter from the perspective of looking backwards up the catheter tube through a distal tip of the catheter (towards a proximal portion of the catheter from the distal tip). Consistent with such examples, ring 915 may be interpreted as corresponding to the distal tip of the catheter. When the catheter is bent, portions of the catheter become visible behind the distal tip (i.e., ring 915). Consequently, bend line 925 may correspond to the portions of the distal end of the catheter that are visible behind the distal tip (i.e., ring 915) due to the bending of the catheter.

In alternative examples, schematic bend representation 910 may include a rendering of the distal end of the catheter from the perspective of looking forward down the catheter tube towards the distal tip from a proximal position along the catheter. Consistent with such examples, ring 915 may be interpreted as corresponding to a cross-sectional cut of the catheter at the proximal position. When the catheter is bent, portions of the distal end become visible behind the cross-sectional cut (i.e., ring 915). Consequently, bend line 925 may correspond to the portions of the catheter that are visible behind the cross-sectional cut (i.e., ring 915) due to the bending of the catheter.

In some examples, bend indicator 900 may display a visual and/or alphanumeric representation of the minimum bend radius or the smallest bend radius detected along the catheter. When the minimum bend radius drops below a threshold value, bend indicator 900 may alert the clinician that the predetermined threshold has been breached by displaying an alphanumeric value and/or may otherwise changing in appearance. In some embodiments, the threshold value may be determined based on whether a tool can be passed through the catheter. In some embodiments, the threshold value may be determined based on the radius at which buckling and/or damage to the catheter may occur. The threshold value may be manually selected, automatically determined, determined based on the type of catheter and/or tool, and/or set using a general rule of thumb. As depicted in FIG. 9, when the minimum detected bend radius is below the threshold value, bend indicator 900 includes a number 920 indicating the real-time value of the minimum bend radius, and portions of bend indicator 900 turn a different color, such as red as shown in FIG. 9. In some embodiments, the location of the red colored portions may reflect the magnitude of the force applied by one of the motor to a catheter pull wire in that section of the catheter. For example, in FIG. 9 the pull wire on the top left is being pulled harder, as indicated by the red colored wedge appearing in schematic bend representation 910. In some examples, bend indicator 900 may include an outer ring 930 that dynamically changes color based whether the minimum bend radius is approaching or exceeds the threshold value. In some examples, dynamic changes could be represented by changes in appearance of portions of the bend indicator 900 in transparency, texture, line width, and/or color etc. Various examples of bend indicators, as well as related indicators for monitoring parameters other than bend, are further described in U.S. Provisional Patent Application No. 62/357,217, which is incorporated by reference above.

Figure 10:
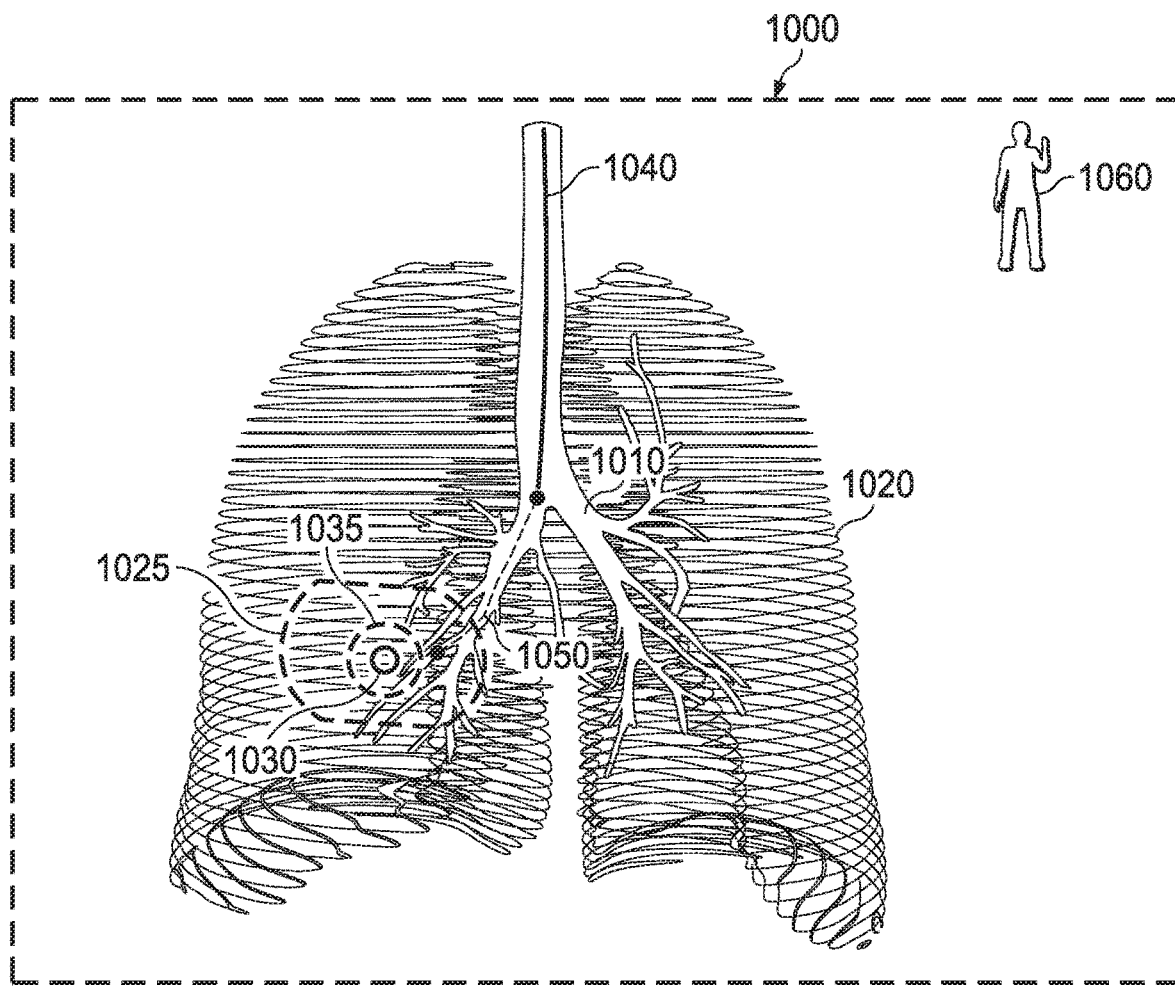
FIG. 10 is a simplified diagram of a global anatomical representation (e.g., a model) according to some embodiments.

FIG. 10 is a simplified diagram of a global anatomical model 1000 according to some embodiments. According to some embodiments consistent with FIGS. 5B-5D, global anatomical model 1000 may correspond to one or more of global anatomical models 513 and/or 514. However, it is to be understood that global anatomical model 1000 may be displayed in contexts other than graphical user interface 500, including as a standalone view and/or in conjunction with views other than those depicted in graphical user interface 500.

Global anatomical model 1000 displays a 3D model 1010 of anatomical passageways. In some examples, 3D model 1010 may be enclosed by a boundary 1020 of the relevant portion of the anatomy (in this case, the lungs). For example, boundary 1020 may be displayed using a translucent fill and/or a wire grid. As depicted in FIG. 10, boundary 1020 is displayed as a horizontal wire grid. The appearance of boundary 1020, (e.g., the color, texture, spacing of the hash marks, and/or the like) may vary to indicate potential hazards. As depicted in FIG. 10, a hazard 1025 corresponds to a portion of boundary 1020 near a target location 1030 that is colored red to alert the clinician to the danger of puncturing the pleura of the lungs when navigating and/or performing interventional steps at target location 1030. In some examples, an uncertainty zone 1035 may appear around target location 1030, e.g., as a semi-transparent sphere as shown in FIG. 10, or in another example in an alternative color. The size of uncertainty zone 1035 may be fixed and/or determined based on one or more factors including the uncertainty in the registered position of the target with respect to the anatomy, the location of the target, the expected difficulty accessing the target, and/or the like. The clinician may use uncertainty zone 1035 to perform interventional steps, such as biopsies, at different distances from the estimated center of the target. For example, when uncertainty zone 1035 is large (e.g., due to a large registration uncertainty), the clinician may be encouraged to take biopsy samples farther away from each other than would otherwise be taken to increase the chance of successfully sampling the lesion.

In some embodiments, global anatomical model 1000 may further include a virtual image of the catheter 1040 based on shape sensing data and/or a planned route 1050 to target location 1050. As depicted in FIG. 10, catheter 1040 is depicted as a green line and planned route 1050 is depicted as a blue line. In some examples, one or more attributes of catheter 1040 (e.g., color, line type, texture, size, etc.) may vary based on measurement data associated with catheter 1040, such as bend radius, temperature, strain, and/or the like. An orientation icon 1060 is located in the upper right to indicate that, in this example, global anatomical model 1010 is viewed from a front perspective. Various examples of global anatomical models are further described in U.S. Provisional Patent Application No. 62/357,217 and U.S. Provisional Patent Application No. 62/357,258, which are incorporated by reference above.

Figure 11A:
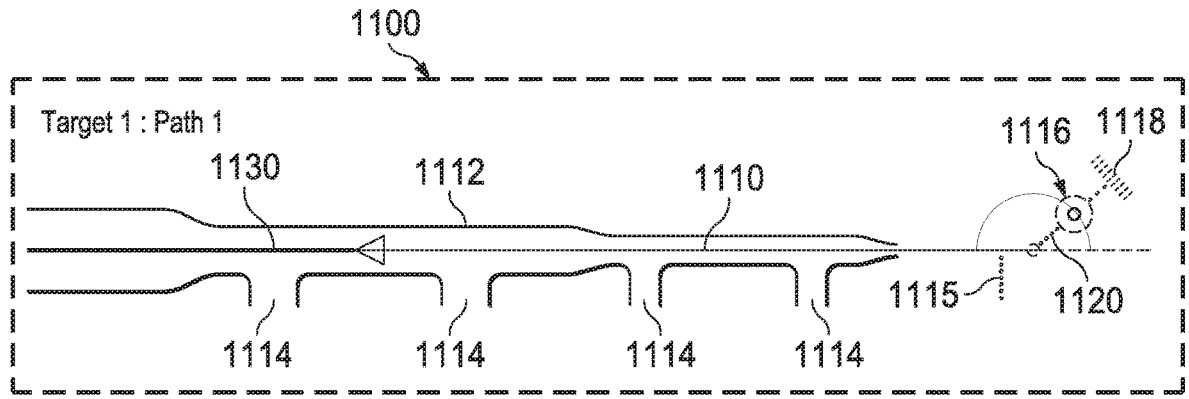
FIGS. 11A-11C are simplified diagrams of a reduced anatomical representation (e.g., a model) at three different times according to some embodiments.
Figure 11B:
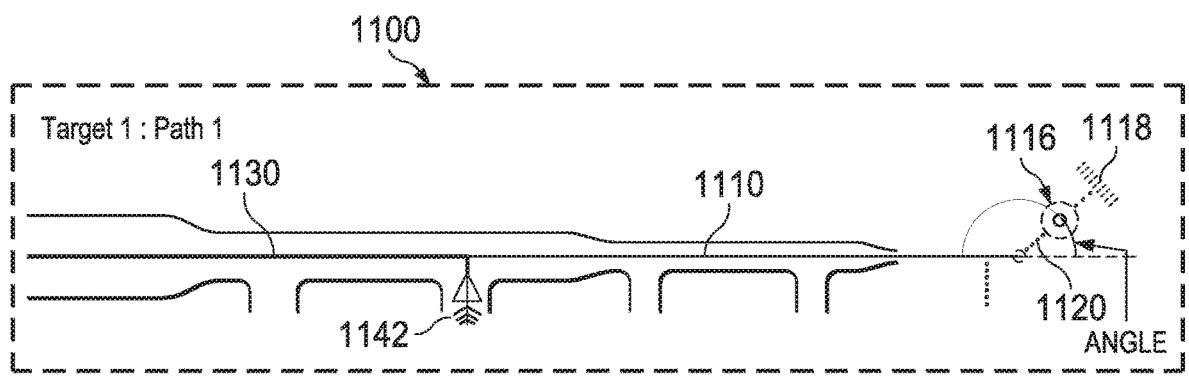
Figure 11C:
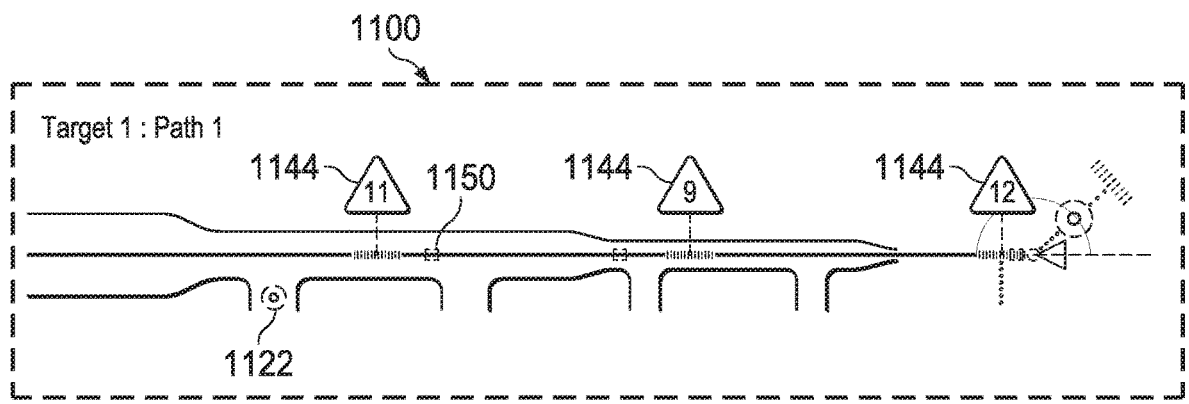

FIGS. 11A-11C are simplified diagrams of a reduced anatomical model 1100 at three different times during a procedure and/or at different catheter locations in the anatomy according to some embodiments. According to some embodiments consistent with FIGS. 5B-5D, reduced anatomical model 1100 may correspond to reduced anatomical model 522. However, it is to be understood that reduced anatomical model 1100 may be displayed in contexts other than graphical user interface 500, including as a standalone view and/or in conjunction with views other than those depicted in graphical user interface 500.

Reduced anatomical model 1100 displays one or more features of the planned route to the target location. As depicted in FIGS. 11A-11C, the features include a simplified route path 1110, the width of a passageway 1112, locations of branched passageways 1114, an alternate route indicator 1115, a target location 1116, a hazard location 1118, and an insertion trajectory 1120. The features may be extracted from a larger anatomical model, such as the full 3D anatomical model used to determine the route during the planning stage. In some examples, reduced anatomical model 1100 may exclude various details from the larger anatomical model.

In some examples, reduced anatomical model 1100 may be displayed as a linear anatomical representation (e.g., a model), in which 3D aspects of the planned route and/or the anatomy are reduced (e.g., straightened, flattened, clipped, resized, simplified, and/or the like) to fit into an elongated area. Consistent with such embodiments, simplified route path 1110 may be represented as a straight line. The width of passageway 1112 is indicated using vertically spaced pairs of horizontal lines centered on simplified route path 1110. In some examples, the width of passageway 1112 may be rounded to a nearest tiered level such that the vertically spaced lines have a tiered spacing generally correlating with generations of branching. Locations of branched passageways 1114 are indicated relative to simplified route path 1110 using horizontally spaced pairs of vertical lines that branch from passageway 1112. In some examples, the full branching structure of branched passageways 1114 (e.g., various sub-branches and/or the 3D shape of branches) may be omitted from reduced anatomical model 1100. For instance, branched passageways 1114 may be displayed as pruned branches that are cut off close to where they intersect with passageway 1112. When a branched passageway provides an alternate route to target location 1116, the passageway may be labeled using alternate route indicator 1115. Rather than depicting the full 3D path of the alternate route, alternate route indicator 1115 may include a simplified indication that an alternate route is available, such as a vertical dotted line. In one example, a clinician can select or click on alternate route indicator 1115. In response, reduced anatomical model 1100 may be updated to display the alternate route, instead of the originally displayed route. In another example, when clinician begins to traverse the branch corresponding to the alternate route, reduced anatomical model 1100 may automatically update to display the alternate route.

Insertion trajectory 1120, representing a puncture trajectory of an instrument through a lumen of passageway 1112, is depicted as a dotted line connecting the end of simplified route path 1110 to target location 1116. When a hazard 1118 (e.g., a blood vessel, large bullae, an organ such as a heart, and/or the pleura of the lung) is located behind and/or otherwise in the vicinity of target location 1116, insertion trajectory 1120 may extend past target location 1116 to indicate the spacing between target location 1116 and hazard 1118, displayed in this example as cross-hatched lines. In some examples, various features including the simplified route path 1110, the branched passageways 1114, the alternate route indicator 1115, the target location 1116, the hazard 1118, and/or the insertion trajectory 1120 can be displayed in a contrasting color, transparency, texture, and/or line width. In general, reduced anatomical model 1100 depicts a single route and target location at a time. When the medical procedure includes multiple target locations, additional target locations may be marked by labeling the corresponding braches through which the additional target locations are reachable using a target icon 1122, as depicted in FIG. 11C.

Reduced anatomical model 1100 is continuously updated to reflect the progress of a catheter 1130 along simplified route path 1110. For example, catheter 1130 may be overlaid on simplified route path 1110 in a contrasting color or shade, such as green. Various indicators and/or alerts may be displayed when anomalies are detected. For example, when catheter 1130 makes a wrong turn, a wrong turn indicator 1142 may appear, as depicted in FIG. 11B. In some examples, bend indicators 1144 may appear when excessive bend is detected. Bend indicators 1144 may include a displayed value representing the bend radius. In some examples, the appearance of catheter 1130 may be modified to draw attention to the tight bend radius, e.g., by changing from a solid green line to a dotted red line. In some examples, one or more bookmarks 1150 may be placed at along the route to indicate locations and/or times of particular interest (e.g., locations where the clinician captured a snapshot and/or otherwise observed interesting features for inspection at a later time). For example, bookmarks 1150 may be depicted as brackets overlaid on catheter 1130.

In some examples, reduced anatomical model 1100 may be displayed in a geometrically constrained area of a graphical user interface. For example, the geometrically constrained area may correspond to a horizontally elongated area, a vertically elongated area, an 'L'-shaped area, and/or various other areas with irregular shapes. The ability to display reduced anatomical model 1100 in a geometrically constrained area may accommodate close packing of reduced anatomical model 1100 with other views of the graphical user interface. Similarly, the ability to fit reduced anatomical model 1100 into geometrically constrained areas may accommodate a display screen with an irregular shape, such as an elongated display screen.

Moreover, reduced anatomical model 1100 may provide the clinician with quick, uncluttered access to information associated with the medical procedure. For example, reduced anatomical model 1100 may display a selected subset of information associated with the medical procedure that is extracted from a more detailed anatomical model. In some examples, reduced anatomical model 1100 may maintain a consistent appearance across different medical procedures. For example, target location 1116 may appear in substantially the same place (e.g., the right-most portion of reduced anatomical model 1100) irrespective of the actual 3D location of the target and/or the actual 3D route to the target. Due to the consistent appearance of reduced anatomical model 1100, the clinician may spend less time searching through and/or comprehending the information displayed in reduced anatomical model 1100 across different medical procedures and/or different routes within a medical procedure.

Figure 12A:
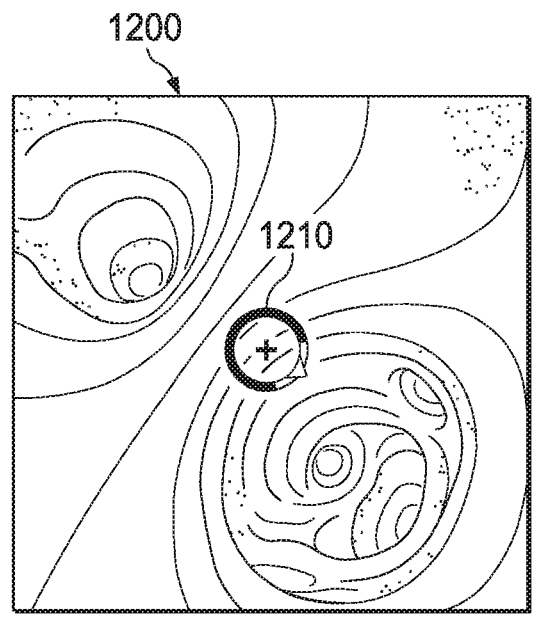
FIGS. 12A-12B are simplified diagrams of a live camera feed at two different times according to some embodiments.
Figure 12B:
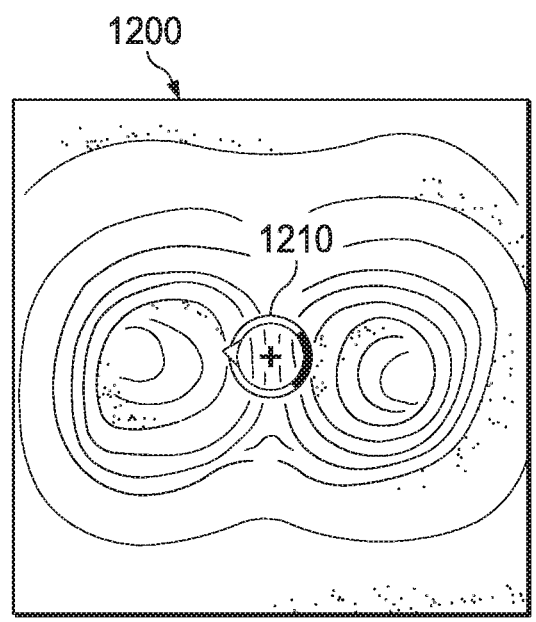

FIGS. 12A-12B are simplified diagrams of a live camera feed 1200 at two different times during a procedure and/or at different catheter locations in the anatomy according to some embodiments. According to some embodiments consistent with FIGS. 5A-5B, live camera feed 1200 may correspond to live camera feed 531. However, it is to be understood that live camera feed 1200 may be displayed in contexts other than graphical user interface 500, including as a standalone view and/or in conjunction with views other than those depicted in graphical user interface 500.

Live camera feed 1200 displays images from a camera, such as an endoscope, at a distal end of the catheter. In some examples, supplemental guidance information 1210 may be overlaid on the camera images. For example, supplemental guidance information 1210 may be generated by identifying features in the images using image processing techniques, by determining the location of the camera in the anatomy using shape data from the catheter, and/or the like. As depicted in FIGS. 12A-12B, supplemental guidance information 1210 is displayed using a reticle that includes a circle with an arrow. As the camera approaches a bifurcation, the arrow points towards the branch that corresponds to the planned route. In some examples, the arrow may appear when the camera approaches a bifurcation and may otherwise be hidden. In some examples, the reticle may be color coded to indicate which branch to steer towards and/or which branch to steer away from. For example, a red portion of the circle may indicate that the catheter should not be navigated down the indicated branch. In another example, the size of the color coded portion may indicate the degree of deviation from the planned path to the target, including a fully red circle when the catheter is in an airway that is not on the path.

FIGS. 13A-13D are simplified diagrams of a virtual distal view 1300 at four different times according to some embodiments. According to some embodiments consistent with FIGS. 5B-5D, virtual distal view 1300 may correspond to virtual distal view 537. However, it is to be understood that virtual distal view 1300 may be displayed in contexts other than graphical user interface 500, including as a standalone view and/or in conjunction with views other than those depicted in graphical user interface 500.

Virtual distal view 1300 is generated based on the 3D model of the anatomy. With the 3D model registered to the anatomy, the position of the catheter within the 3D model may be determined based on real time shape sensing. Virtual distal view 1300 is then generated by rendering the 3D model from the perspective of the distal end of the catheter (i.e., the distally looking viewpoint).

In some examples, the rendered 3D model images may include supplemental guidance information 1310. Like supplemental guidance information 1210, supplemental guidance information 1310 may include one or more direction indicators in various forms to help navigate branches. For example, the correct branch may be indicated by lighting up (or otherwise altering the appearance of) the branch to be driven down, providing a line showing which branch to drive down, displaying a reticle similar to FIGS. 12A-12B, and/or the like. In another example, the view may contain a reticle in the center of the view to assist in precisely aiming the direction of the catheter, e.g. to align it with the center of the target. In the examples depicted in FIGS. 13A, the branch to be driven down is highlighted using contour lines that selectively extend down the correct branch. In some embodiments, a blocking indicator (e.g., a stop sign, do not enter sign, and/or the like) may appear over an incorrect branch. Additionally, virtual distal view 1300 can include a target distance indicator 1320 and a hazard distance indicator 1330. Target distance indicator 1320 can provide the distance from the distal end of the catheter to the target. Hazard distance indicator 1330 can provide the distance from the distal end of the catheter to a nearest hazard, such as the pleura, the heart, large bullae, and/or blood vessels. Various examples of virtual distal views are further described in U.S. Provisional Patent Application No. 62/357,258, which is incorporated by reference above.

Figure 13A:
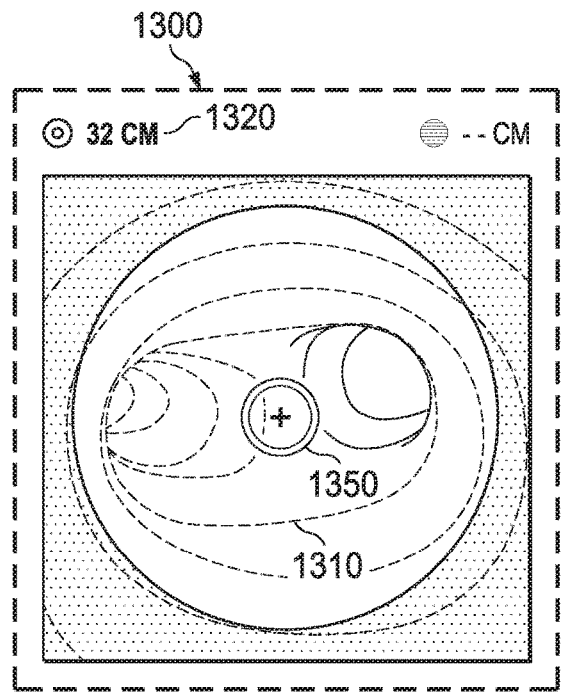
FIGS. 13A-13D are simplified diagrams of a virtual distal view at two different times according to some embodiments.
Figure 13B:
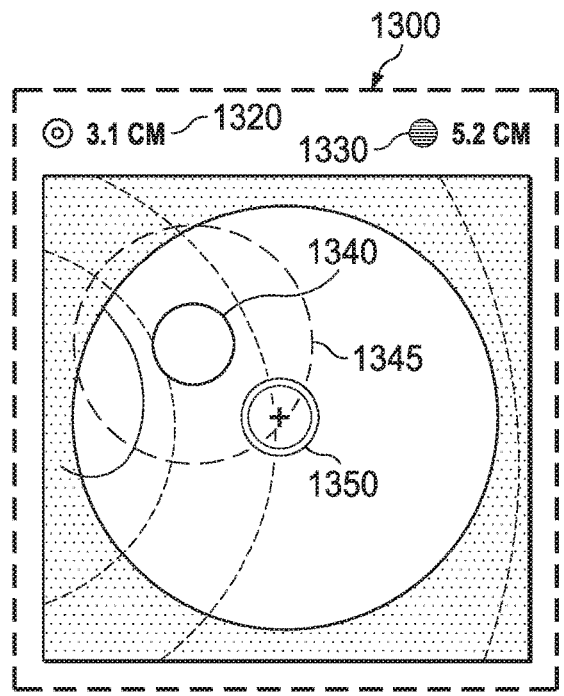

When the catheter is positioned within a predetermined threshold distance from the target, the appearance and/or configuration of virtual distal view 1300 can transition to provide directional guidance towards the target. In particular, the target may be embedded within the passageway wall relative to the distal end of the catheter and thus not visible as shown in FIG. 13A. FIG. 13B displays an example of the virtual distal view when the distal end of the catheter is positioned within a threshold distance to the target, as indicated by the distance to target indicator 1320. In this example, 3.1 cm is within a threshold where the appearance of virtual distal view 1300 is modified to display the passageway walls as transparent (or semi-transparent such) that a target is visible. In other examples, the threshold distance can vary based on procedure, type of tool, target size, target location, etc. As shown in FIG. 13B, the target is shown as a semi solid sphere 1340 while an uncertainty zone 1345 is shown as a semi-transparent sphere. Additionally, a cross hair 1350 can be provided which indicates the direction the catheter is facing. In some examples, cross hair 1350 indicates the location an instrument, such as a biopsy needle, would puncture if inserted through a central lumen of the catheter. As shown in FIG. 13B, cross hair 1350 includes a circle and a cross in the center of the circle. In alternative embodiments, cross hair 1350 could include only a circle with a small dot in the center. Cross hair 1350 could be automatically centered in the view such that the view is always showing the distal view from the catheter centered in the image. In one example, cross hair 1350 would always be displayed showing the center forward facing direction of the catheter. In alternative examples, cross hair 1350 would automatically appear as the catheter approaches the target within a pre-defined threshold. In even further examples, the user could provide an input to display or hide cross hair 1350 as desired.

Figure 13C:
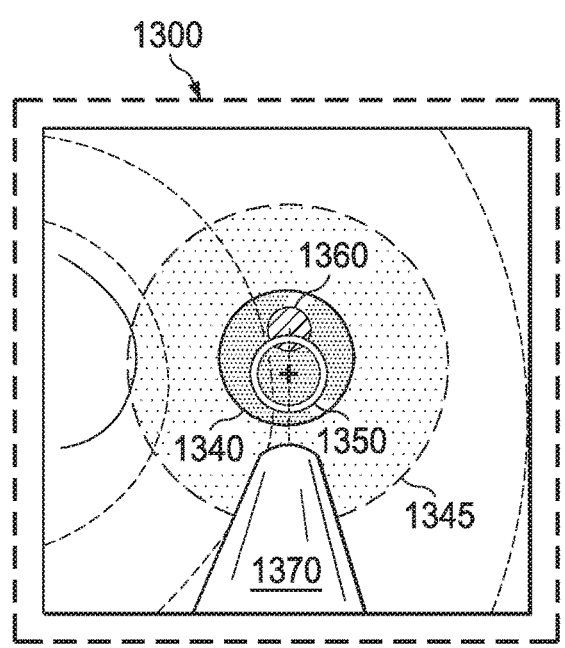

FIG. 13C displays an alternative example of the virtual distal view 1300, which is similar to the view of FIG. 13B, showing the target 1340, the uncertainty zone 1345, the cross hair 1350, and additionally providing a view of a hazard 1360. In the example of FIG. 13C a virtual image of the catheter 1370 is also displayed. In alternative embodiments the catheter image 1370 is not shown.

Figure 13D:
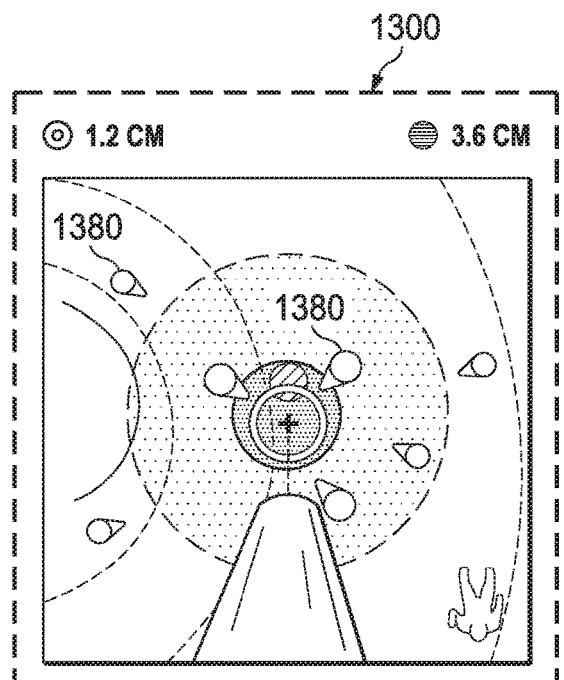

FIG. 13D displays another example of the virtual distal view 1300 that can be displayed during a medical procedure such as a biopsy. Virtual distal view 1300 as depicted in FIG. 13D can be similar to those previously described, with the exception of providing a dynamic representation of interventional steps previously performed during the medical procedure. As shown in FIG. 13D, after a series of biopsies have been performed, the virtual distal view can dynamically update to indicate the various locations of each biopsy using labels 1380. This can aid the user in choosing the next biopsy location. While the example in FIG. 13D is described for a biopsy procedure, it should be understood that the virtual distal view 1300 can be used to show historical applications of any type of procedure including therapeutic procedures such as ablation, chemical therapy and/or any other type of diagnostic procedure. In some examples, additional labels corresponding to labels 1380 may be updated in various other views of graphical user interface 500, such as the global anatomical models 513, 514 shown in FIG. 5B.

Figure 14:
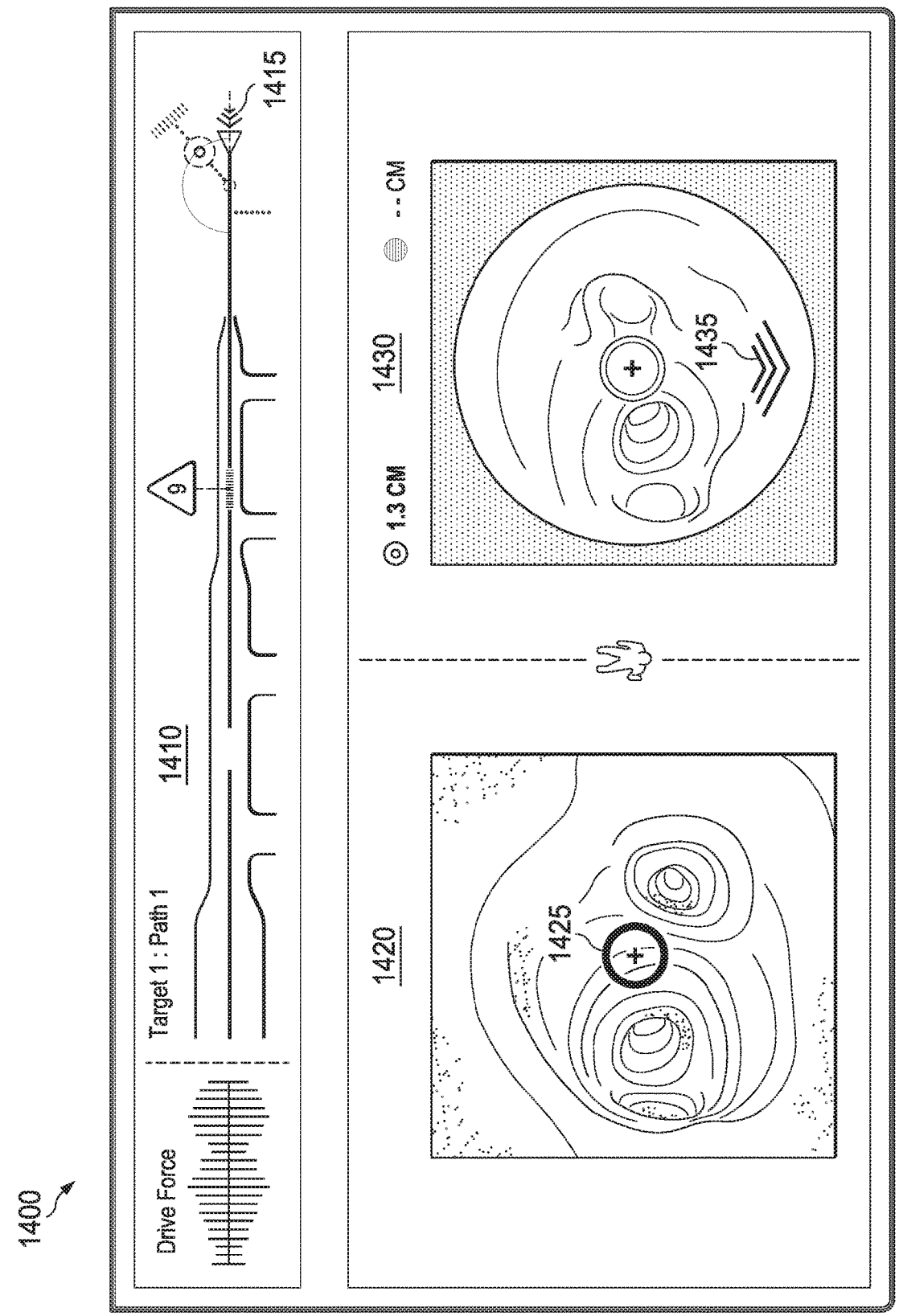
FIG. 14 is a simplified diagram of a set of views during a scenario in which a catheter is inserted beyond the end of the planned route according to some embodiments.

FIG. 14 is a simplified diagram of a set of views 1400 during a scenario in which a catheter is inserted beyond the end of the planned route according to some embodiments. Views 1400 include a reduced anatomical view 1410, a live camera feed 1420, and a virtual distal view 1430. These generally correspond to similarly labeled views depicted in FIGS. 5-13B. Views 1400 illustrate various techniques for alerting the clinician that the catheter has been inserted beyond the end of the route and should be withdrawn. In reduced anatomical view 1410, a reverse indicator 1415 appears at the distal end of catheter. In live camera feed 1420, a reticle 1425 turns fully red to indicate that none of the branches that appear in the image are correct. In virtual distal view 1430, the contour lines disappear and a reverse indicator 1435 appears. It is to be understood that these alerting measures are merely illustrative, and many other signaling techniques may be used to alert the clinician that the catheter has been inserted beyond the end of the route.

Figure 15A:
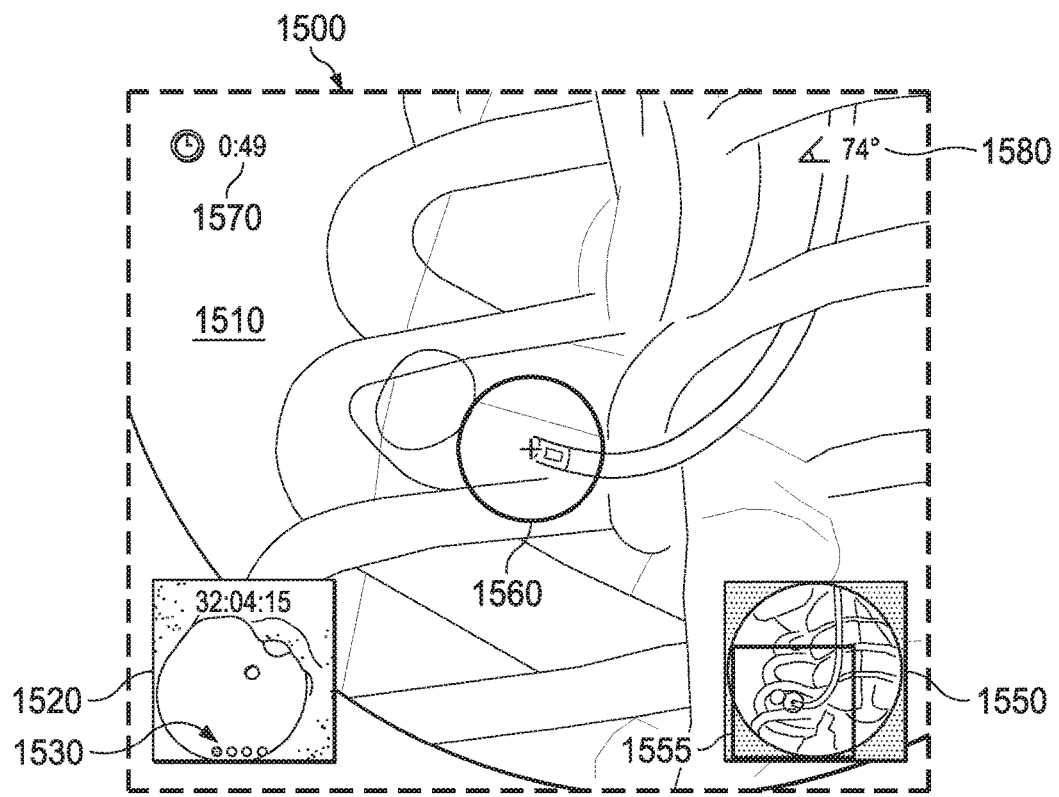
FIGS. 15A-15C are simplified diagrams of a remote image view in a plurality of modes according to some embodiments.
Figure 15B:
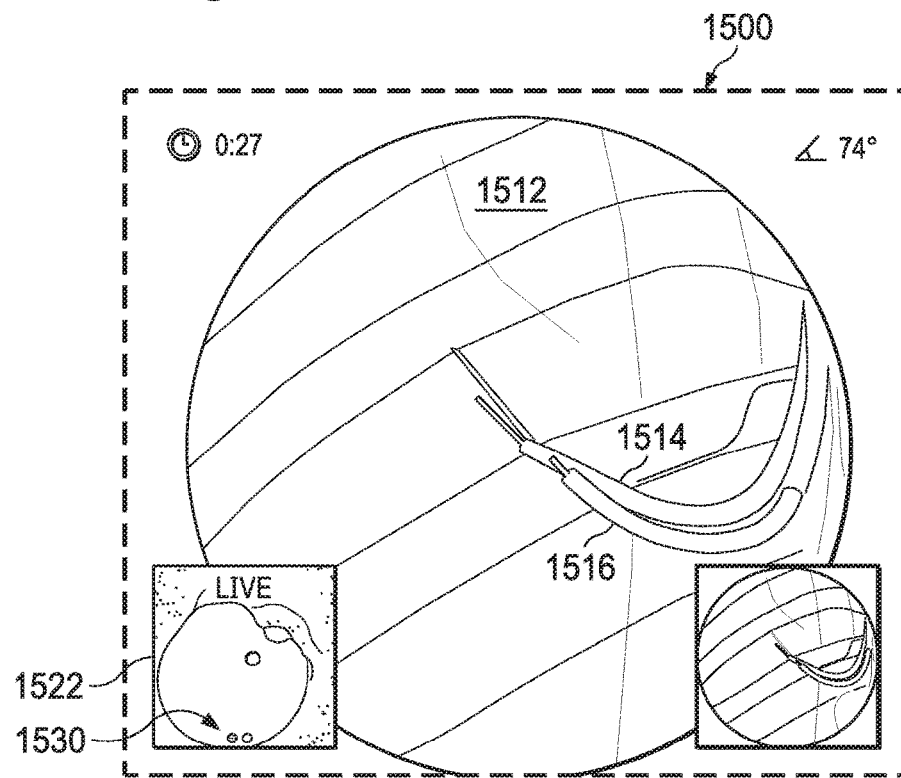
Figure 15C:
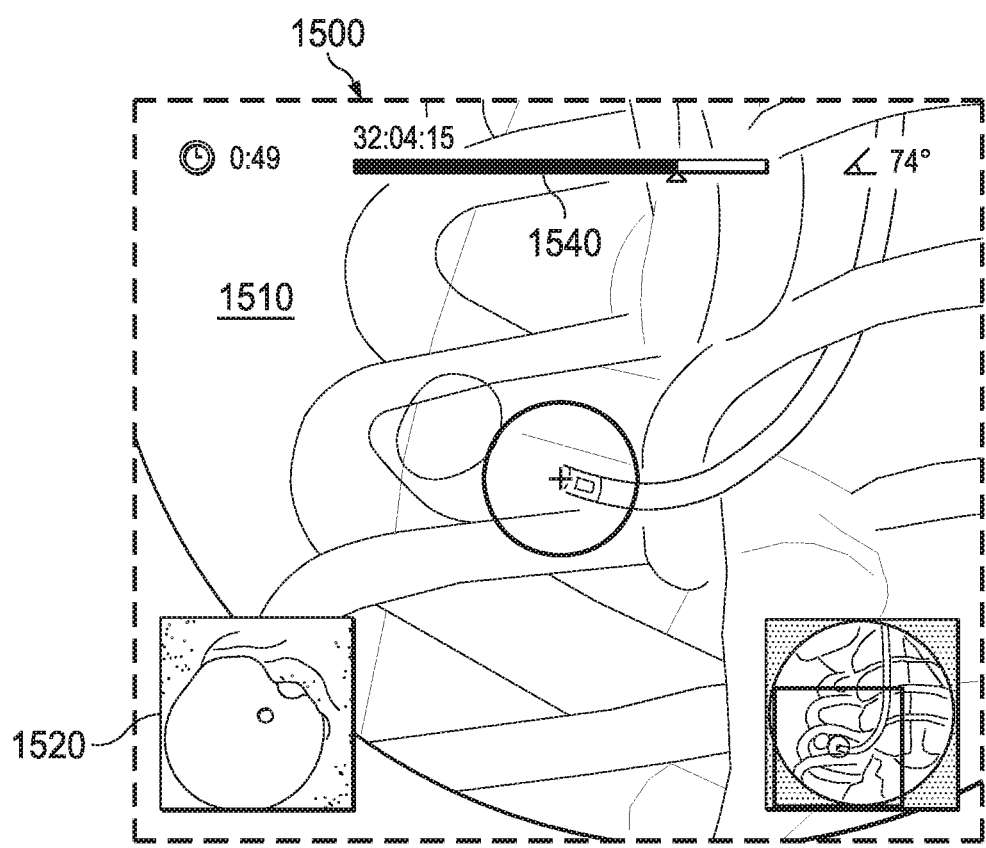

FIGS. 15A-15C are simplified diagrams of a remote image view 1500 in a plurality of modes according to some embodiments. According to some embodiments consistent with FIG. 5D, remote image view 1500 may correspond to remote image view 538. However, it is to be understood that remote image view 1500 may be displayed in contexts other than graphical user interface 500, including as a standalone view and/or in conjunction with views other than those depicted in graphical user interface 500.

FIG. 15A illustrates remote image view 1500 in a live mode. In the live mode, remote image view 1500 displays a live remote image 1510, such as a fluoroscopy image, of the relevant portion of the anatomy (e.g., the lungs). Live remote image 1510 can be adjusted to zoom in, zoom out, pan the view of the image, and/or the like. The clinician can provide an input through a remote controller or use a mouse or scroll ball to drag the live image of the fluoroscopic view. In addition, if the system is connected to a mechanically adjustable fluoroscopic arm, the system can rotate the fluoroscopic arm to provide an alternative live remote image 1510, one that perhaps provides a better view of the target or catheter. In addition, remote image view 1500 displays a live probe image 1520 from the distal end of the catheter, such as an image generated by an endoscope and/or EBUS probe. The clinician may adjust the position of the catheter while monitoring live remote image 1510 and/or live probe image 1520. At various point during the live mode, the clinician may capture and save snapshots of one or more images displayed in remote image view 1500. Thus, a series of snapshots may be saved over time as the probe is re-positioned while attempting to locate and/or align the catheter to the target location. Once satisfied with the alignment, the clinician may remove the probe from the catheter system and replace with a tool for performing an interventional step, such as a biopsy needle. In some examples, the tool may not include an imaging functionality, so the clinician can no longer monitor live probe image 1520. Accordingly, one or more of the saved snapshots may be used as a reference when live probe images are no longer available.

FIG. 15B illustrates remote image view 1500 in a reference mode. In some examples, remote image view 1500 includes a reference selection indicator 1530 to indicate which snapshot is being used as the reference. As indicated in FIG. 15A-15B, reference selection indicator 1530 includes a series of dots. When the left-most dot is highlighted, remote image view 1500 is in the live mode. Selecting one of the dots on the right indicates that remote image view 1500 is in the reference mode. Each dot corresponds to a different saved snapshot. In this regard, the clinician may scroll through the saved snapshots and select one as the reference. When the reference is selected, live probe image 1520 is replaced with a previously captured probe image 1522 from the saved snapshot. Furthermore, a previously captured remote image 1512 from the saved snapshot is overlaid on live remote view. As depicted in FIG. 15B, a catheter image 1514 included in previously captured remote image 1512 appears as a blue "shadow" relative to a catheter image 1516 included in the grayscale live remote view 1510. In this regard, the clinician may observe differences between previously captured remote image 1512 and live remote image 1510. For example, as depicted in FIG. 15B, the clinician may determine the catheter has shifted downward relative to the reference because the "shadow" (catheter image 1514) is offset from the real-time position of the catheter (catheter image 1516). To the extent that the clinician desires for the position of the catheter to match that of the reference, the clinician may proceed to steer the catheter upward until live remote image 1510 matches previously captured remote image 1512.

FIG. 15C illustrates remote image view 1500 in a timeline mode. Instead of and/or in addition to displaying reference selection indicator 1530 to scroll through snapshots during reference selection, remote image view 1500 the timeline mode may include a timeline 1540 for scrolling among continuously and/or periodically saved snapshots. In this regard, the clinician may rewind the medical procedure to determine the desired reference. As depicted in FIG. 15C, when the selected time is the present time (i.e., real-time), the configuration of remote image view 1500 is similar the live mode depicted in FIG. 15A. When the clinician scrolls back to a prior time using timeline 1540, remote image view 1500 transitions to a configuration similar to the reference mode depicted in FIG. 15B.

Referring back to FIG. 15A, live remote image 1510 may correspond to a portion of a zoomed out image 1550. The clinician may select the portion of zoomed out image 1550 that is displayed in live remote image 1510 by drawing, resizing, and/or moving a box 1555 in zoomed out image 1550 that represents the portion displayed in live remote image 1510. The clinician may perform the selection using mouse clicks, gestures, multi-finger gestures, and/or the like. These selection methods may apply to a touch screen displaying remote image view 1500, an external touch screen, and/or another suitable input device. Various indicators may also be displayed in remote image view 1500. As depicted in FIGS. 15A-15C, the indicators include a timer and fluoroscopy angle indicator on live remote image 1550, and a time stamp on live probe image 1520 (and/or on timeline 1540).

A clinician may place a marker 1560 over a portion of live remote image 1510 to tag features and/or to detect shifts in position over time. In the example depicted in FIGS. 15A and 15C, the clinician may align the catheter with the target location using a probe inserted into the catheter. When the catheter is aligned, the clinician may place marker 1560 over the distal end of the catheter. Subsequently, the probe may be removed from the catheter and replaced with a tool for performing an interventional step, such as a biopsy needle. In some examples, the tool may not include an imaging functionality, so the clinician can no longer monitor live probe view 1510 to achieve alignment. Assuming the fluoroscopy image does not move when replacing the probe with tool, however, the clinician may use marker 1560 to confirm that the catheter is at substantially the same location and is thus remains aligned with the target location.

In some examples, a timer 1570 may be displayed to indicate the amount of elapsed time since the clinician started the time. Timer 1570 may, for example, be used to track the duration of a breath hold, or the duration of the procedure, or otherwise. Timer 1570 may be started and/or stopped manually by the physician and/or automatically when certain events are measured by the system, such as detection of the start and stop of a breath hold. Timer 1570 may change appearance (e.g., color, font, size, texture, etc.) to alert the clinician to hazardous conditions, such as the elapsed time exceeding a predetermined threshold (e.g., one minute). In some examples, an orientation icon 1580 may be displayed to indicate the perspective of live remote image 1510. In the case of a fluoroscopy image, orientation icon 1580 may indicate the angle setting of the fluoroscopy imager.

Figure 16:
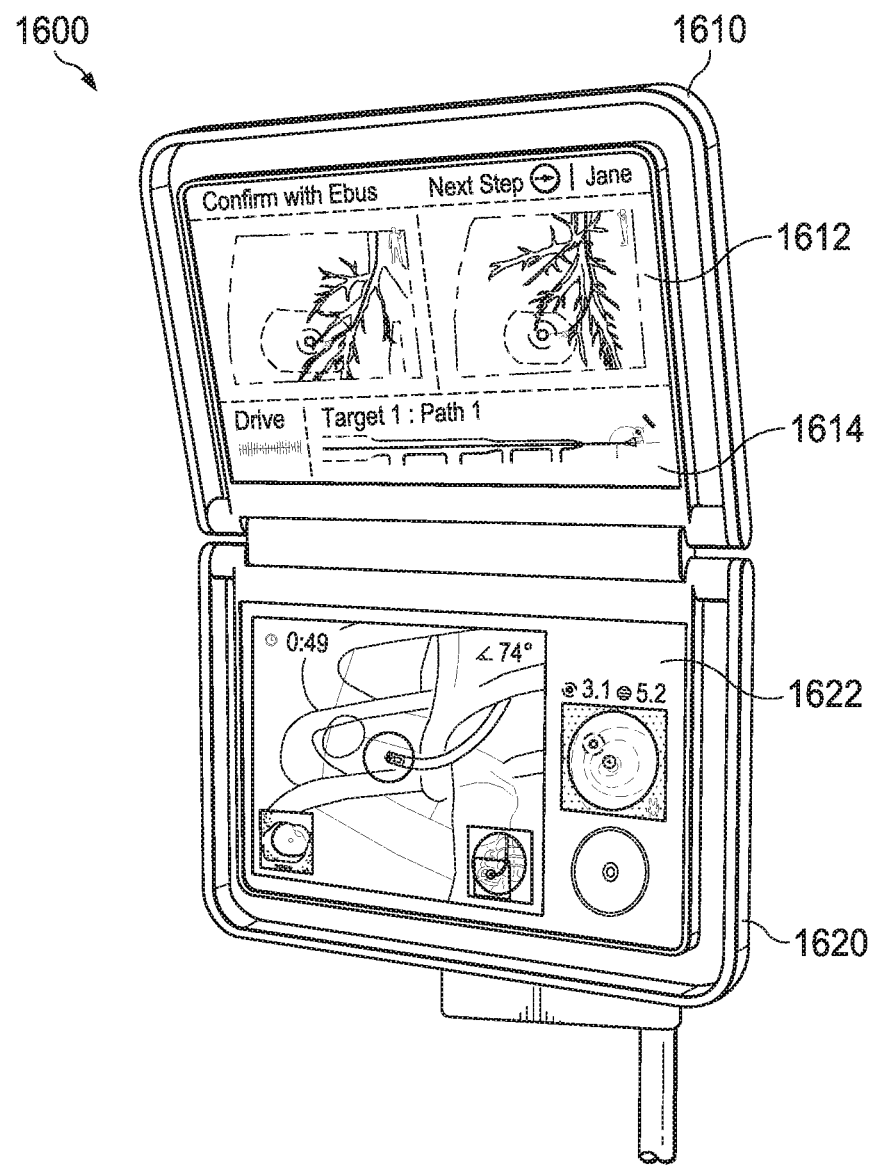
FIG. 16 is a simplified diagram of a dual-screen display for displaying a graphical user interface according to some embodiments.

FIG. 16 is a simplified diagram of a dual-screen display 1600 for displaying a graphical user interface, such as graphical user interfaces 400 and/or 500, according to some embodiments. In some embodiments, dual-screen display 1600 may be included in display system 110. As depicted in FIG. 16, dual-screen display 1600 is vertically split into an upper screen 1610 and a lower screen 1620. Upper screen 1610 and lower screen 1620 are approximately the same size, such that dual-screen display 1600 is foldable along the vertical split. Upper screen 1610 displays one or more global views 1612 and one or more compact views 1614, and lower screen 1620 displays one or more local views 1622. These views generally correspond to similarly labeled views in FIGS. 4-5D. In the example depicted in FIG. 16, the graphical user interface is in a performance mode, such that the views generally correspond to those of FIG. 5D. However, it is to be understood that dual-screen display 1600 may also be used to render the graphical user interface in the registration mode, as depicted in FIG. 5A, the navigation mode, as depicted in FIG. 5B-5C, and/or the like. In one example, one or both of screens 1610 and/or 1620 may be touchscreens which can be manipulated by the user to alter views including rotating views, zooming, panning, switching between views, etc. In an alternative example, the screens in FIG. 16 are provided for viewing and a separate touchscreen and/or user input device can be used to alter views.

FIG. 17 is a simplified diagram of a method 1700 for monitoring a medical procedure according to some embodiments. According to some embodiments consistent with FIGS. 1-16, method 1700 may be used to operate graphical user interface 500 in a plurality of modes including a registration mode, a navigation mode, and a performance mode.

At a process 1710, in a registration mode of the graphical user interface and during registration of an anatomical model to a patient anatomy, registration progress information is displayed via the graphical user interface. In some embodiments, the registration mode of the graphical user interface may correspond to the registration mode of graphical user interface 500, as depicted in FIG. 5A. In some embodiments, the registration progress information may be displayed using a dynamic point cloud view, such as dynamic point cloud view 600. In some embodiments, the registration progress information may be displayed using a dynamic registration guidance view, such as dynamic registration guidance view 700.

At a process 1720, when the anatomical model is registered to the patient body, the graphical user interface transitions from the registration mode to a navigation mode. In some embodiments, the graphical user interface may transition automatically in response to detecting that registration is complete. In some embodiments, a clinician may manually cause graphical user interface to transition from the registration mode to the navigation mode. For example, the clinician may click a button that appears in the registration mode of the graphical user interface.

At a process 1730, in the navigation mode and during navigation of an elongate device through the patient anatomy to a target location, navigation progress information is displayed via the graphical user interface. In some embodiments, the navigation mode of the graphical user interface may correspond to the navigation mode of graphical user interface 500 as depicted in FIG. 5B. In some embodiments, the navigation progress information may be displayed using a global anatomical model, such as global anatomical model 1000. In some embodiments, the navigation progress information may be displayed using a reduced anatomical model, such as reduced anatomical model 1100.

In some embodiments, the navigation progress information may be displayed using a live camera feed augmented by supplemental guidance information, such as live camera feed 1200. In some embodiments, the navigation progress information may be displayed using a virtual distal view augmented by supplemental guidance information, such as virtual distal view 1300.

At a process 1740, when the elongate device is in the proximity of the target location, the graphical user interface transitions from the navigation mode to a performance mode. In some embodiments, the graphical user interface may transition automatically in response to detecting that the elongate device is within a threshold distance of the target location. In some embodiments, a clinician may manually cause graphical user interface to transition from the navigation mode to the performance mode. For example, the clinician may click a button that appears in the navigation mode of the graphical user interface.

At a process 1750, in the performance mode and during performance of an interventional step at the target location, performance progress information is displayed via the graphical user interface. In some embodiments, the performance mode of the graphical user interface may correspond to the performance mode of graphical user interface 500 as depicted in FIG. 5D. In some embodiments, the performance progress information may be displayed using one or more views similar to those displayed at process 1730, including the global anatomical model, the reduced anatomical model, and/or the virtual distal view. In some embodiments, the performance progress information may be displayed using a remote image view, such as remote image view 1500. In some embodiments, one or more probes may be inserted into the elongate device after the elongate device has been navigated to the target location and before performing the medical procedure. The one or more probes, which may include an endoscope, and EBUS probe, and/or the like, may be used to fine-tune the alignment of the elongate device to the target location and/or to capture one or more reference images. Subsequently, the one or more probes may be removed and replaced with a tool for performing the interventional step, such as a biopsy needle. When the tool for performing the interventional step is inserted into the elongate device, the one or more reference images may be used to confirm that the elongate device remains aligned with the target location. The clinician may scroll among the one or more reference images to select which reference image to use. Once the reference image is selected, a differential image may be displayed to highlight differences between the live remote image and the reference image. Based on the differences, the clinician may adjust the alignment of the elongate device to cause the live remote image to match the reference image. When the alignment is satisfactory, the interventional step may be performed.

In some embodiments, method 1700 may terminate after process 1750. In some embodiments, method 1700 may proceed back to process 1730 to navigate the elongate device to one or more additional target locations. In other embodiments, method 1700 may proceed back to process 1710 to repeat and/or attempt to improve registration. At any process of method 1700, the graphical user interface may alert the clinician to a detected anomaly, in which case the clinician may correct the anomaly, terminate the medical procedure, revert to a previous step, and/or proceed in spite of the anomaly.

FIG. 18 is a simplified diagram of a method 1800 for monitoring a medical procedure using a graphical user interface according to some embodiments. According to some embodiments consistent with FIGS. 1-16, method 1800 may be used to generate and/or display one or more views of graphical user interface 500, including reduced anatomical model 522 and/or 1100.

At a process 1810, a route to a target location in a patient anatomy is received. In some embodiments, the route may be determined during a planning stage of the medical procedure. The route may subsequently be transferred to a medical instrument system capable of performing the medical procure at the target location, such as medical instrument system 200. In some examples, the route may define a path through airways in the lungs to a target location in the lungs. In some examples, the target location may include one or more of a lesion, a nodule, a tumor, and/or the like.

At a process 1820, one or more features of the route are extracted from or determined based on a first anatomical model. In some embodiments, the first anatomical model may include a full model of known passageways in the relevant portion of the patient anatomy. For example, the first anatomical model may include a model of lung airways that was used to determine the route during the planning of the medical procedure. In some examples, the first anatomical model may include an anatomical model that is registered to the patient anatomy and displayed in a global anatomical model view, such as global anatomical model view 1000. In some examples, the extracted features may include a simplified path of the route, such as a straight line representation of the route.

In some examples, the extracted features may include landmark features that the clinician is expected to encounter when navigating a medical instrument, such as a catheter, along the route. In some examples, the landmark features may include a simplified map of anatomical passageways that branch from the route (e.g., a set of bifurcations encountered when traversing the route). For example, the simplified map may include indicate locations of the anatomical passageways that branch from the route, rather than a complete branching structure of the passageways. The locations may be indicated using annotations marking the location of the branches, such as clipped branches (as depicted in FIGS. 11A-11C), dots, hash marks, and/or the like. In some example, the simplified map may include a target icon when one or more second target locations are reachable via the corresponding branched passageway. Other landmark features may include lesions, nodules, blood vessels, discolorations, and/or various other notable features encountered along the route.

In some embodiments, the extracted features may include a width of the passageway along the route. In some examples, the width may be represented using a tiered format. For example, the width may be rounded to the nearest tiered level and/or may be approximated based on the branching generation of the passageway at a given position. In some embodiments, the extracted features may include the target location and/or the position of one or more hazards in the vicinity of the target location. In some examples, the extracted features may include an insertion trajectory (e.g., an angle of insertion) from the end of the route to the target location.

At a process 1830, a reduced anatomical model is generated based on the one or more extracted features of the route. In some examples, the reduced anatomical model may be significantly simpler, smaller, and/or clearer than the first anatomical model because the most relevant features of the first anatomical model are included while various less relevant details are excluded. In some examples, the extracted features may be flattened, straightened, clipped, simplified, and/or the like during generation of the reduced anatomical model.

At a process 1840, real-time position information associated with a medical instrument is received during the medical procedure. According to some embodiments, the medical instrument may include a steerable catheter with a localization sensor, such as a shape sensor. Consequently, the real-time position information may include shape data from the shape sensor. Various other real-time information associated with the medical procedure and/or the medical instrument, such as temperature data, strain data, and/or the like may also be received at process 1840. Receiving the real-time position information may also include determining one or more anomalies in the real-time position information. For example, excessive bending of the catheter, overheating, excessive drive force, and/or the like may be determined at process 1840.

At a process 1850, the real-time position information is associated with (e.g., via mapping to) the reduced anatomical model. In some examples, mapping the real-time position information to the reduced anatomical model may include determining how far along the simplified route path the medical instrument extends. In some examples, one or more anomalies, such as a wrong turn and/or extending beyond the end of the simplified route path may be determined at process 1850.

At a process 1860, the reduced anatomical model with the real-time position information is dynamically displayed. In examples consistent with FIG. 11, the display may correspond to reduced anatomical model 1100. The displayed size of the reduced anatomical model may be set in different ways, e.g. adjusted to always fit the full width of the available screen space, and/or be sized to correlate with the physical length of the path (i.e. a longer path may be displayed in a larger view than a shorter path). When an anomaly is detected in the real-time progress information, such as the anomalies determined at processes 1840 and/or 1815, the display may include one or more indicators to alert the clinician to the anomaly. In some examples, when the anomaly includes steering the medical instrument down an incorrect passageway, the one or more indicators may include a wrong turn indicator. When the anomaly includes driving the instrument beyond the end of the route, the one or more indicators may include a reverse indicator. When the anomaly includes a tight bend radius, the one or more indicators may include an excessive bend indicator and/or may include modifying the appearance (e.g., the color, line style, and/or the like) of the medical instrument as depicted in the reduced anatomical model. After process 1860, method 1800 may return to process 1840 to continuously receive, map, and dynamically display real-time position information on the reduced anatomical model.

Figure 19:
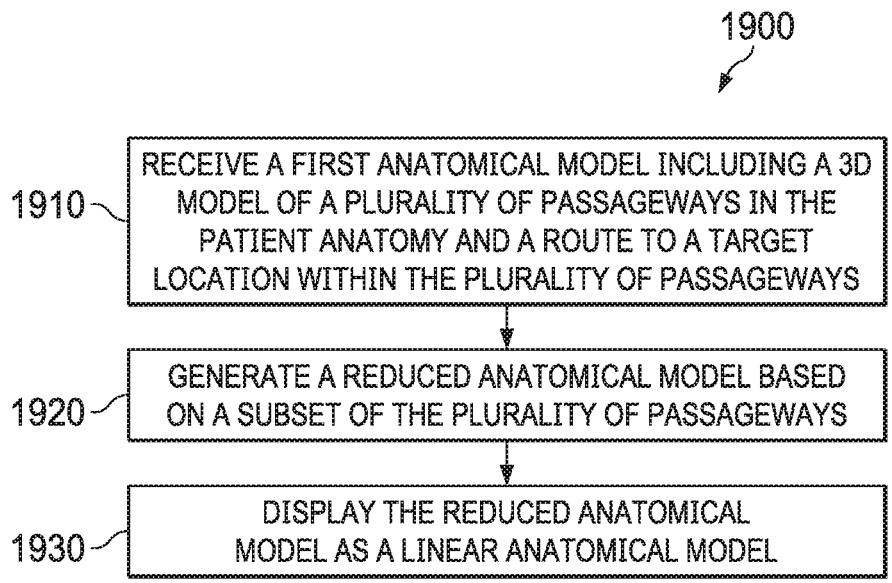
FIG. 19 is a simplified diagram of a method for displaying a patient anatomy using a graphical user interface according to some embodiments.

FIG. 19 is a simplified diagram of a method 1900 for displaying a patient anatomy using a graphical user interface according to some embodiments. According to some embodiments consistent with FIGS. 1-16, method 1900 may be used to generate and/or display one or more views of graphical user interface 500 and/or portions thereof, including reduced anatomical model 522 and/or 1100.

At a process 1910, a first anatomical including a 3D model of a plurality of passageways in the patient anatomy and a route to a target location within the plurality of passageways is received. In some examples, the patient anatomy may correspond to lungs. Consistent with such examples, the plurality of passageways may correspond to airways of the lungs. In some examples, the target location may include a legion, a nodule, a tumor, and/or the like.

At a process 1920, a reduced anatomical model is generated based on a subset of the plurality of passageways. The subset of passageways include path passageways that are directly connected to the route. That is, the path passageways include the subset of passageways that would be encountered (e.g., passed through and/or entered) by a medical instrument, such as a catheter, when traversing the route.

At a process 1930, the reduced anatomical model is displayed as a linear anatomical model. In some examples, a width of the path passageways may be represented using vertically spaced lines having a tiered separation. For example, the tiered separation may be tiered down (i.e., the vertically spaced lines are brought closer together) for path passageways having a higher branching generation. For instance, in the case of lungs, path passageways close to the trachea have a low branching generation and accordingly are depicted using vertically spaced lines with a wide separation, whereas path passageways near the end of the route (e.g., after having traversed multiple branching points along the route) may have a high branching generation and accordingly may be tiered down one or more times relative to the path passageways close to the trachea. In some examples, the locations of branches off the path passageways may be represented in the linear anatomical model. Because branched passageways may not be directly connected to the route, the branches may be represented as clipped branches without representing their full branching structure (e.g., various sub-branches).

Figure 20:
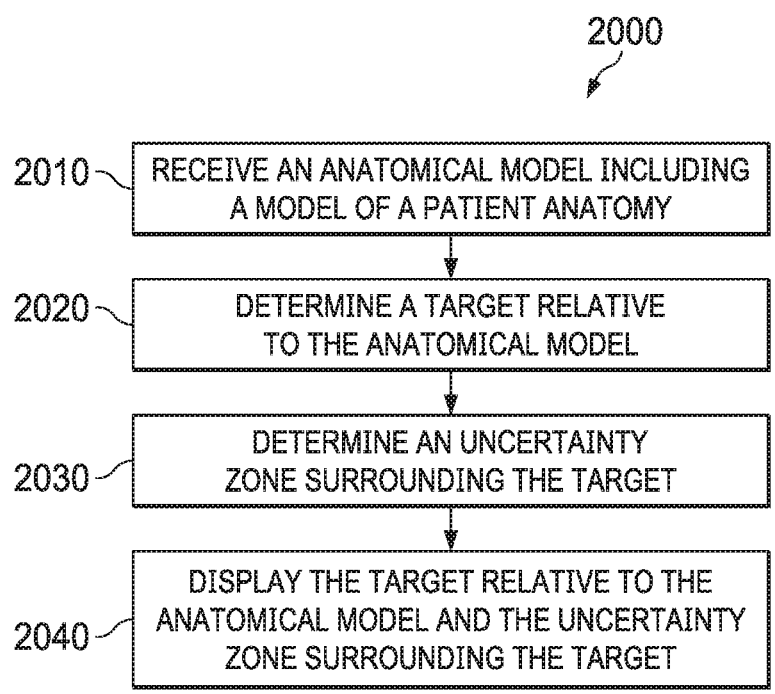
FIG. 20 is a simplified diagram of a method for displaying a target within a patient anatomy using a graphical user interface according to some embodiments.

FIG. 20 is a simplified diagram of a method 2000 for displaying a target within a patient anatomy using a graphical user interface according to some embodiments. According to some embodiments consistent with FIGS. 1-16, method 2000 may be used to generate and/or display one or more views of graphical user interface 500 and/or portions thereof, including virtual endoscopic view 1300.

At a process 2010, an anatomical model including a model of a patient anatomy is received. For example, the anatomical model may be a 3D model of a patient's lungs that includes a model of the airways of the lungs. At a process 2020, a target is determined relative to the anatomical model. For example, the target may include a predetermined size and/or location of a lesion, tumor, nodule, and/or the like. At a process 2030, an uncertainty zone surrounding the target is determined. In some examples, the uncertainty zone may be determined based on a registration uncertainty associated with registering the anatomical model to the patient anatomy. In some examples, the uncertainty zone may be determined based on the size of the target. In some examples, the uncertainty zone may be determined based on an expected difficulty to access the target (i.e., a hard-to-reach target may be subject to greater uncertainty). At a process 2040, the target and the uncertainty zone surrounding the target are displayed relative to the anatomical model. In some examples, such as when the target and/or uncertainty zone are outside of the passageways of the anatomical model, the passageways of the anatomical model may be rendered in a translucent manner such that the target and uncertainty zone are visible through the walls of the passageways.

Some examples of control units, such as control unit 130 may include non-transient, tangible, machine readable media that include executable code that when run by one or more processors (e.g., processor 140) may cause the one or more processors to perform the processes of methods 1700-2000 and/or to render graphical user interfaces 400 and/or 500. Some common forms of machine readable media that may include the processes of methods 1700-2000 and/or the instructions for rendering graphical user interfaces 400 and/or 500 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A medical device comprising:
an elongate device including a flexible body;
a tracking system disposed along at least a portion of the flexible body;
one or more processors communicatively coupled to the tracking system;
wherein the one or more processors are configured to:
receive a route to a target location in an anatomy, the route traversing a plurality of tiers of passageways of the anatomy;
determine one or more features of the route based on a first anatomical representation;
generate an elongated, linear reduced anatomical representation based on the one or more features of the route, the elongated, linear reduced anatomical representation including a passageway width for each tier of the plurality of tiers of passageways along the route, wherein the passageway width for each tier is constant along a length of each tier;
receive real-time position information from the tracking system;
associate the real-time position information to the elongated, linear reduced anatomical representation; and
dynamically display the elongated, linear reduced anatomical representation with the associated real-time position information.

2. The medical device of claim 1, wherein the anatomy corresponds to lungs, and wherein the first anatomical representation includes a plurality of passageways in the anatomy that correspond to airways of the lungs.

3. The medical device of claim 1, wherein the one or more features of the route include locations of branches along the route.

4. The medical device of claim 3, wherein the locations of the branches in the elongated, linear reduced anatomical representation include clipped branches without a full branching structure of the branches.

5. The medical device of claim 3, wherein an alternative route indicator is displayed to represent an alternative route to the target location.

6. The medical device of claim 1, wherein the one or more features of the route include a hazard associated with the route.

7. The medical device of claim 1, wherein dynamically displaying the real-time position information includes displaying one or more indicators when an anomaly is detected.

8. The medical device of claim 7, wherein the one or more indicators includes one or more of a wrong turn indicator, a reverse indicator, or an excessive bend indicator.

9. A method for displaying an anatomy, the method comprising:
providing a graphical user interface;
receiving a first anatomical representation comprising a 3D representation of a plurality of passageways in the anatomy and a route to a target location within the plurality of passageways, the route traversing a plurality of tiers of passageways of the anatomy;
generating an elongated, linear reduced anatomical representation based on a subset of the plurality of passageways wherein the subset of the plurality of passageways comprises path passageways directly connected to the route, the elongated, linear reduced anatomical representation including a passageway width for each tier of the plurality of tiers of passageways along the route, wherein the passageway width for each tier is constant along a length of each tier; and
displaying the elongated, linear reduced anatomical representation.

10. The method of claim 9, wherein the anatomy corresponds to lungs, and wherein the plurality of passageways in the anatomy correspond to airways of the lungs.

11. The method of claim 9, wherein the target location includes one or more of a lesion, a nodule, or a tumor.

12. The method of claim 9, wherein locations of branches off the path passageways are included in the elongated, linear reduced anatomical representation.

13. The method of claim 9, further comprising displaying an alternative route indicator representing an alternative route to the target location.

14. The method of claim 9, further comprising displaying an insertion trajectory from an end of the route to the target location.

15. The method of claim 14, further comprising identifying a hazard associated with the route and displaying a location of the hazard relative to the insertion trajectory.

16. The method of claim 9, further comprising:
receiving real-time position information associated with an instrument during traversal of the route;
mapping the real-time position information to the elongated, linear reduced anatomical representation; and
dynamically displaying the real-time position information with the elongated, linear reduced anatomical representation.

17. The method of claim 16, wherein dynamically displaying the real-time position information includes displaying one or more indicators when an anomaly is detected.

18. The medical device of claim 1, wherein each tier of the plurality of tiers includes a different passageway width.

19. The method of claim 9, wherein each tier of the plurality of tiers includes a different passageway width.

* * * * *

UNITED STATES PATENT AND TRADEMARK OFFICE
CERTIFICATE OF CORRECTION

| | | |
|---|---|---|
| PATENT NO. | : 11,937,880 B2 | |
| APPLICATION NO. | : 16/499575 | |
| DATED | : March 26, 2024 | |
| INVENTOR(S) | : Vincent Duindam et al. | |

It is certified that error appears in the above-identified patent and that said Letters Patent is hereby corrected as shown below:

In the Specification

Column 7, Line 32, change "(MM)" to -- (MRI) --

Signed and Sealed this
Twenty-first Day of May, 2024

Katherine Kelly Vidal
*Director of the United States Patent and Trademark Office*